(12) United States Patent
Grimm et al.

(10) Patent No.: US 12,275,722 B2
(45) Date of Patent: Apr. 15, 2025

(54) PROCESS OF REWORKING A CRYSTALLINE FORM OF A GLYCINE TRANSPORT INHIBITOR

(71) Applicant: Boehringer Ingelheim International GmbH, Ingelheim am Rhein (DE)

(72) Inventors: Julia Regina Grimm, Mainz (DE); Katrin Baer, Mainz (DE); Albert Josef Barta, Warthausen (DE); Gisela Bodenbach, Niederburg (DE); Joe Ju Gao, Southbury, CT (US); Fredrik Lars Nordstrom, Ridgefield, CT (US); Michael Wiese, Gensingen (DE); Bing-Shiou Yang, Southbury, CT (US); Manabu Nakatani, Hyogo (JP); Masashi Adachi, Mino (JP); Kenji Egusa, Ikeda (JP); Roman Christian Messerschmid, Wiesbaden (DE); Daniela Maria Schroeder, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 470 days.

(21) Appl. No.: 17/498,027

(22) Filed: Oct. 11, 2021

(65) Prior Publication Data
US 2022/0112183 A1    Apr. 14, 2022

(30) Foreign Application Priority Data
Oct. 13, 2020    (EP) .................................... 20201550

(51) Int. Cl.
*C07D 413/04* (2006.01)
*A61K 9/20* (2006.01)
*A61K 31/422* (2006.01)

(52) U.S. Cl.
CPC .......... *C07D 413/04* (2013.01); *A61K 9/2013* (2013.01); *A61K 9/2018* (2013.01); *A61K 9/2054* (2013.01); *A61K 9/2095* (2013.01); *A61K 31/422* (2013.01); *C07B 2200/13* (2013.01)

(58) Field of Classification Search
None
See application file for complete search history.

(56) References Cited

U.S. PATENT DOCUMENTS

| | | |
|---|---|---|
| 6,673,799 B1 | 1/2004 | Taniguchi |
| 7,220,744 B2 | 5/2007 | Jolidon et al. |
| 7,317,125 B2 | 1/2008 | Bolin et al. |
| 7,332,495 B2 | 2/2008 | Li et al. |
| 7,473,787 B2 | 1/2009 | McHardy et al. |
| 7,557,114 B2 | 7/2009 | Jolidon et al. |
| 7,951,836 B2 | 2/2011 | Bertani |
| 8,188,139 B2 | 5/2012 | Jolidon et al. |
| 8,288,435 B2 | 10/2012 | Aissaoui et al. |
| 8,497,289 B2 | 7/2013 | Lindsley et al. |
| 8,816,079 B2 | 8/2014 | Maeda et al. |
| 2006/0167000 A1 | 7/2006 | Barnham et al. |
| 2008/0107334 A1 | 5/2008 | Tsai |
| 2008/0287455 A1 | 11/2008 | Jolidon et al. |
| 2010/0035914 A1 | 2/2010 | Bertani et al. |
| 2012/0022099 A1 | 1/2012 | Zlotnikov et al. |
| 2015/0087673 A1 | 3/2015 | Hitoshi et al. |

FOREIGN PATENT DOCUMENTS

| | | |
|---|---|---|
| CN | 1381449 A | 11/2002 |
| CN | 104628679 A | 5/2015 |
| CN | 107540636 A | 1/2018 |
| EP | 1396487 A1 | 3/2004 |
| EP | 2556829 A1 | 2/2013 |
| JP | 2008239568 A | 10/2008 |
| JP | 2013107881 A | 6/2013 |
| WO | 2000017163 A1 | 3/2000 |
| WO | 2001044181 A1 | 6/2001 |
| WO | 2002008221 A2 | 1/2002 |
| WO | 2004089363 A1 | 10/2004 |
| WO | 2005011653 A2 | 2/2005 |
| WO | 2005014563 A1 | 2/2005 |
| WO | 2005037216 A2 | 4/2005 |
| WO | 2006044174 A2 | 4/2006 |
| WO | 2006106425 A1 | 10/2006 |
| WO | 2007053394 A1 | 5/2007 |
| WO | 2008107334 A2 | 9/2008 |
| WO | 2009016560 A2 | 2/2009 |
| WO | 2009139576 A2 | 11/2009 |
| WO | 2010059239 A2 | 5/2010 |
| WO | 2010078348 A1 | 7/2010 |
| WO | 2010080357 A1 | 7/2010 |
| WO | 2010116328 A2 | 10/2010 |
| WO | 2010150281 A2 | 12/2010 |
| WO | 2011136292 A1 | 11/2011 |

(Continued)

OTHER PUBLICATIONS

Chaudhari, Pharma Excipients, A review, Int J. advances in pharma, biology, and chemistry, vol. 1, 2012, p. 21-34.
European Search Report for EP2020150.9 mailed Apr. 6, 2021.
Caira, Crystalline polymorphism of organic compunds, Topics in current chem., vol. 198, 1998.
Seo, Combined TRPC3 and TRPC6 blockade by selective small-molecule or genetic deletion inhibits pathological cardiac myopathy, PNAS, 2013.
Sharma, Review of Transient Receptor Potential Canonical Channel Modulators, Jour. of Medicinal Chem, 2019.

(Continued)

*Primary Examiner* — Tigabu Kassa
(74) *Attorney, Agent, or Firm* — David L. Kershner

(57) ABSTRACT

The invention describes a process for reworking of a crystallization product comprising drying and homogenization. The crystallization product is crystalline [5-(methylsulfonyl)-2-{[(2R)-1,1,1-trifluoropropan-2-yl]oxy}phenyl]{(1R,5R)-1-[5-(trifluoromethyl)-1,2-oxazol-3-yl]-3-azabicyclo[3.1.0]hex-3-yl}methanone. The product is dried in a tray dryer or in a pan dryer and subsequently homogenized.

7 Claims, 16 Drawing Sheets

(56) References Cited

FOREIGN PATENT DOCUMENTS

| WO | 2011143365 A1 | 11/2011 |
|---|---|---|
| WO | 2012016217 A1 | 2/2012 |
| WO | 2012037349 A2 | 3/2012 |
| WO | 2012158784 A2 | 11/2012 |
| WO | 2013017657 A1 | 2/2013 |
| WO | 2013057124 A1 | 4/2013 |
| WO | 2013059146 A1 | 4/2013 |
| WO | 2013066714 A1 | 5/2013 |
| WO | 2014139144 A1 | 9/2014 |
| WO | 2014191336 A1 | 12/2014 |
| WO | 2015048547 A2 | 4/2015 |
| WO | 2015083179 A1 | 6/2015 |
| WO | 2015101957 A2 | 7/2015 |
| WO | 2016027275 A1 | 2/2016 |
| WO | 2016073774 A2 | 5/2016 |
| WO | 2016138114 A1 | 9/2016 |
| WO | 2016138144 A2 | 9/2016 |
| WO | 2017222930 A1 | 12/2017 |
| WO | 2018159827 A1 | 9/2018 |
| WO | 2018170225 A1 | 9/2018 |
| WO | 2018183145 A1 | 10/2018 |
| WO | 2019023198 A1 | 1/2019 |
| WO | 2019046931 A1 | 3/2019 |
| WO | 2020223419 A1 | 11/2020 |

OTHER PUBLICATIONS

Sieber, Devleopment of a scalable, chromatogrpahy-free synthesis of a t-Bu-SMS-Phos and Application to the synthesis of an important chiral CF-3-Alcohol derivative, The J. of Organic Chem., vol. 83, 2018, 4 pages.
Song, Critical Role of TRPC6 channels in the development of Human renal cell carcinoma, Mol. Biol Rep, 2013.
Tauseef, TLR4 activation of TRPC6-dependent calcium dignaling mediates endotoxin-induced lung vascular permeability, J. of Experimental Med, 2009.
Thilo, Pulsatile Atheroprone Shear Stress Affects the Expression of Transient Receptor Potential Channels in Human Endothelial Cells, Dept. of Nephrology, 2012.
Thilo, VEGF regulates TRPC6 channels in podocytes, Nephrol Dial Transplant, 2012.
Toader, Schitz Bulletin, Effects of Metabotropic Glutamate, 2019 Abstracts, 2 pages.
Urban, Identificationand Validation of Larixyl Acetate as a potent TRPC6 inhibitor, Molecular Pharma, 2015.
Wang, Effects of chronic exposure to cigarette smoke on canonical transient receptor potential expression in rat pulmonary arterial smooth muscle, Am. J. Cell Physiol 2013.
Washburn, The discovery of potent blovkers of the canonical transient receptor Channels, Bioorganic & Medicinal Chem. Letters, 2013, p. 4979-4984.
Weissman, Activation of TRPC6 channels is essential for lung ischamia-reperfusion induced oedema in mice, Nature Communications, 2011.
Wen, Regulation of Multi-drug Resistance in hepato cellular carcinoma cells is TRPC6/Calcium delendent, Nature, 2015.
Winn, A mutation in the TRPC6 Cation Channel causes Familial focal Segmental Glomerulosclerisi, Sciene Mag.org, vol. 38, 2005.
Written Opinion for PCT/US2019/017939 mailed May 15, 2019.
Wu, TRPC channels are necessary mediators of patholgic cardic hypertropy, PNAS, 2010.
Xiaowen, Pharmacy Classroom Notes, 2011, p. 222.
Xie, Cardioprotection by Klotho through downregulation of TRPC6 channels, Nature Communications, 2012.
Xie, Soluble Kloto protects against Uremic cradiomyopahy indepndently of Fibroblast growth Factor 23 and Phophate, JASN, 2015.
Yu, Enhanced expression of transient receptor potential channels of idiopathic pulmonary arterial hypertension, PNAS, 2004.
Zhang, High expression of transient potential rceptor C6 correclated with poor prgonosis in pateients with esophageal squamous cell carcinmoa, Med. oncol, 2013.
Zhang, Micro-RNA-26a prevents endotherial cell apoptosis by directly targeting TRPC6 in the setting of atherosclerosis, Nature, 2015.
Abstract in English for WO2009139576 published Nov. 19, 2009.
Alessandri, TRPC1 and TRPC6 Channels Cooperate with TRPV4 to Mediate Mechanical Hyperalgesia and Nociceptor Sensitization, THe journal od Neuroscience, 2009, vol. 29, p. 6217-6228.
Antigny, Transient Receptor Potential Canonical Channel 6 Links, Institut de Psysiologie, vol. 44, 2011.
Baldovini et al., 3-Oxa- and 3-Azabicyclo[3.1.0]hexan-2-ones via Tandem Radical Cydlization-Intramolecular SN2 Reactions, J of Organic Chemistry, 1996, vol. 61, p. 3205-3208.
Bergdahl, Plasticity of TRPC expression in arterial smooth muscle, Am J. Physiol vol. 22, 2004.
Chigrupati, Receptor Channel TRPC6 is a key mediator of Notch Driven Glioblastoma Growth and Invasiveness, Tumor and Stem cell Biology, 2009.
Clapham, The TRP Ion channel Family, Nature, 2001.
Clarson, Store Operated CA2 entry in first trimester and term human placenta, J. Psysiol, 2003.
Clinical Trials, NCT02832037, Clinical Trial of BI425809 Effect on Cognition and Functional Capacity in Schizophrenia, A phase II Randomised, Double Blind, Placebo controlled Parallel group trial, May 20, 2020, 6 pages.
CN103360343 abstract cited herein, 2013.
CN104628679 abstract cited.
Davis, A TRPC6-dependent pathway for myofibroblast transdifferentiation and wound healing in vivo, Dev. cell, 2012.
Desai, TRP channels and mice deficient in channels, Eur, J, Physiol, 2005.
Ding, Essential Role of TRPC6 Channels in G2M Phase Transition and Development of Human Glioma, Oxford Univ. Press, 2010.
Ding, Pyrazolo [1,5-a] pyrimidine TRP6 antagonists, Cancer Letters, 2018.
Dutille, High Expression of Trasient Receptor Potential Channels in Human Breast Cancer Epithelial Cells and Tissues, Cell Physiol Biocehem, 2011.
Eckel, TRPC6 Enhances Angiotensin II-induced Albunieria, JASN, 2011.
Finney-Hayward, Expression of Transient Receptor Potential C6 Channels in Human Lung Macrophages, American Journal of Respiratory cell and Molecular Biol, 2010.
Frutos, Development of a scalable, asymmetric process for the synthesis of GLYT1 inhibitor BI 425819, OPR&D, vol. 27, 2023, p. 505-512.
Gilligan et al., Divergent mechanisms for the Dealkoxycarbonylation of a 2-(3-Azetidiny)malonate by Chloide and Cyanide, Tetrahedron Letters, 1994, vol. 35, No. 21, pp. 3441-3444.
Hafner, A Larixol Congener with High Affinity and Subtype Selectivity toward TRP6, ChemPubSoc Europe, 2018, vol. 13, p. 1028-1035.
Hofman, Direct Activation of human TRPC6 and TRPC3 channels by diacylglycerol, Letters to Nature, 1999.
Holz, Investigational Treatment for Cognitive Impairment Associated with Schizophrenia receives FDA Breakthrough therapy designation, Press Release, BI, from May 24, 2021.
International Search Report and Written Opinion for PCT/EP2018/079276 mailed Oct. 25, 2018.
International Search Report and Written Opinion for PCT/EP2018079276.
International Search Report and Written Opinion for PCT/EP2019/053525 mailed Apr. 10, 2019.
International Search Report for PCT/EP2023/072960 received Jan. 5, 2024.
International Search Report, Mailed May 15, 2019 for PCT/US2019/017939.
International Search Report, PCT/ISA/210, and Written Opinion, form PCT/ISA/237, for corresponding application PCT/EP2012/065140, date of mailing Aug. 27, 2012.

(56) References Cited

OTHER PUBLICATIONS

Iyer, Receptor Channel TRPC6 orchestrate the activation of human hepatic stellate cell under hypoxia condition, Experimental Cell Research, 2015.
Johannson, Cebrovascular endothelin I hyperreactivity is associated with transient receptor potential canonical channels 1 and 6 activation and delayed cerebral hypoperfusion after forebrain iscachemia in rats, Acta Pysiol, 2015.
Krall, Podocyte-Specific Overexpression of Wild-Type or Mutalnt TRPC6 in Mice, PLOS One, 2010.
Ku, Expression of Transient ReceptorChannel Proteins, J. Soc Gynol Testing, 2006.
Kunichika, Bosentan Inhibiits Transient Receptor Potential Channel Expression in Pulmonary Vascular Myocytes, Amer. J. of Respiratory and Critical Care Medicine, 2004.
Kuwahara, TRPC6 fulfills a calcineurin signalling circuit during pathologic cardiac remodelling, Journal of Clincal Investigation, 2006.
Lei, The role of mechanical tension on lipid raft dependent PDGF-induced TRPC6 activation, Biomaterials, 2014.
Matsuoka, Masakuni "Advances Crystallization Technology for Organic Materials: Control of Size, Morphology, Polymorph and Purity" (2003) Pharm Tech Japan, vol. 19, No. 6, 91-101.
Mayer, Discovery and Pharmacological characterization of a novel potent inhibitor, British Jour. of Phamra, 2015.
Medda et al., 3,4-Methano-ß-Proline: A Conformationally Constrained ß-Amino Acid, Synlett, vol. 2009, No. 6, p. 921-924.
Moller, Induction of TRPC6 Channel in Acquired Forms of Proteneuric Kidney Disease, J. Am. Socio Nephrol. 2007.
Moschetti, Safety, Tolerability and Pharmacokinetics of Oral BI 425809, Eur. J. Drug Pharmcokinetics, vol. 43, 2018, 11 pages.
Moschetti, Safety, Tolerability, and Pharmacokinetics of Oral BI 425809, a-Glycine Transporter 1 Inhibitor, in Healthy male volunteers: Eur. J. Drug Metab Pharmacokinet. vol. 43, 2018, p. 239-249.
Motoyama, Discovery of a bicyclo [4.3.0] nonane DS88790512 as a potent, selective, and orally bioavailable blovker of transient receptor potential canonical 6, Bioorganic & Medicinal Chem letters, 2018, p. 2222-2227.
Pinard, Selective GlyT1 inhibitors: Discovery of {4-(3-Fluoro-5-trifluromethylpyridin-2-yl)piperazin-1-yl}-[5-methanesulfonyl-2-((S-2,2,22-trifluoro-1-methylethoxy)phenyl]methanone (RG1678), a promising Novel medicine to treat Schizophrenia, J. Med. Chem, vol. 53, 2010, p. 4603-4614.
Quiros, Identifcation of TRPC6 as a possible candidate target gene within an amplicon at 11q21-q22.2 for migratory capacity in head and neck squamos cell carcinomas, BMC cancer, 2013.
Reiser, TRPC6 is a glomerular slit diaphragm-associated channel required for normal renal function, Nature genetics, 2005.
Rosenbaum, Hypercholesterolemia inhibits re-endotheliaization of arterial injuries by TRPC channel activation, Journal of Vascular Surgery, 2014.
Rosenbrock, Evaluation of Pharmacokinetics and Pharmacodynamics of BI 425809, Clin. Trasl Sci., vol. 11, 2018, p. 616-623.
Sadowski, A single gene cause in 29.5 of cases of steroid resistant nephrotic syndrome, JASN, 2014.
Schlondorff, TRPC6 mutations associated with focal segmental glomerulosclerosis cause constitutive actication of NFAT-dependent transciptioin, Am. J. Cell Physiol. 2009.

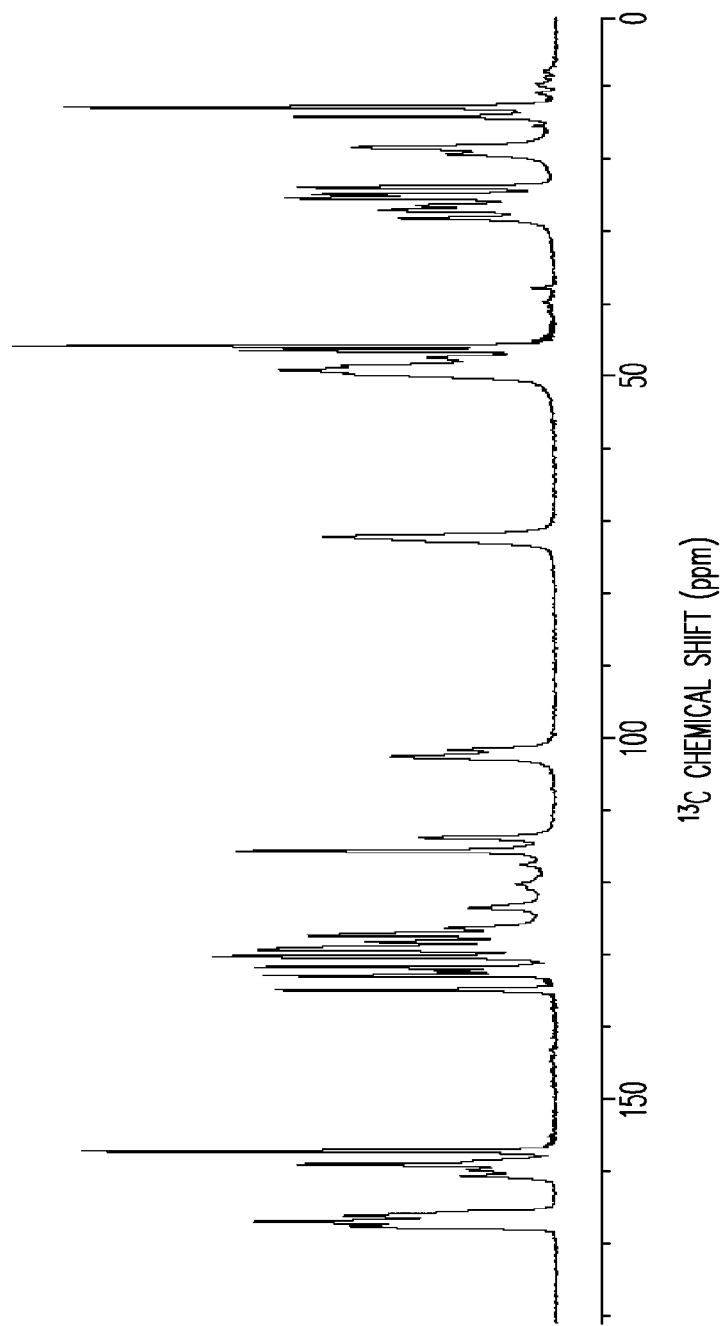

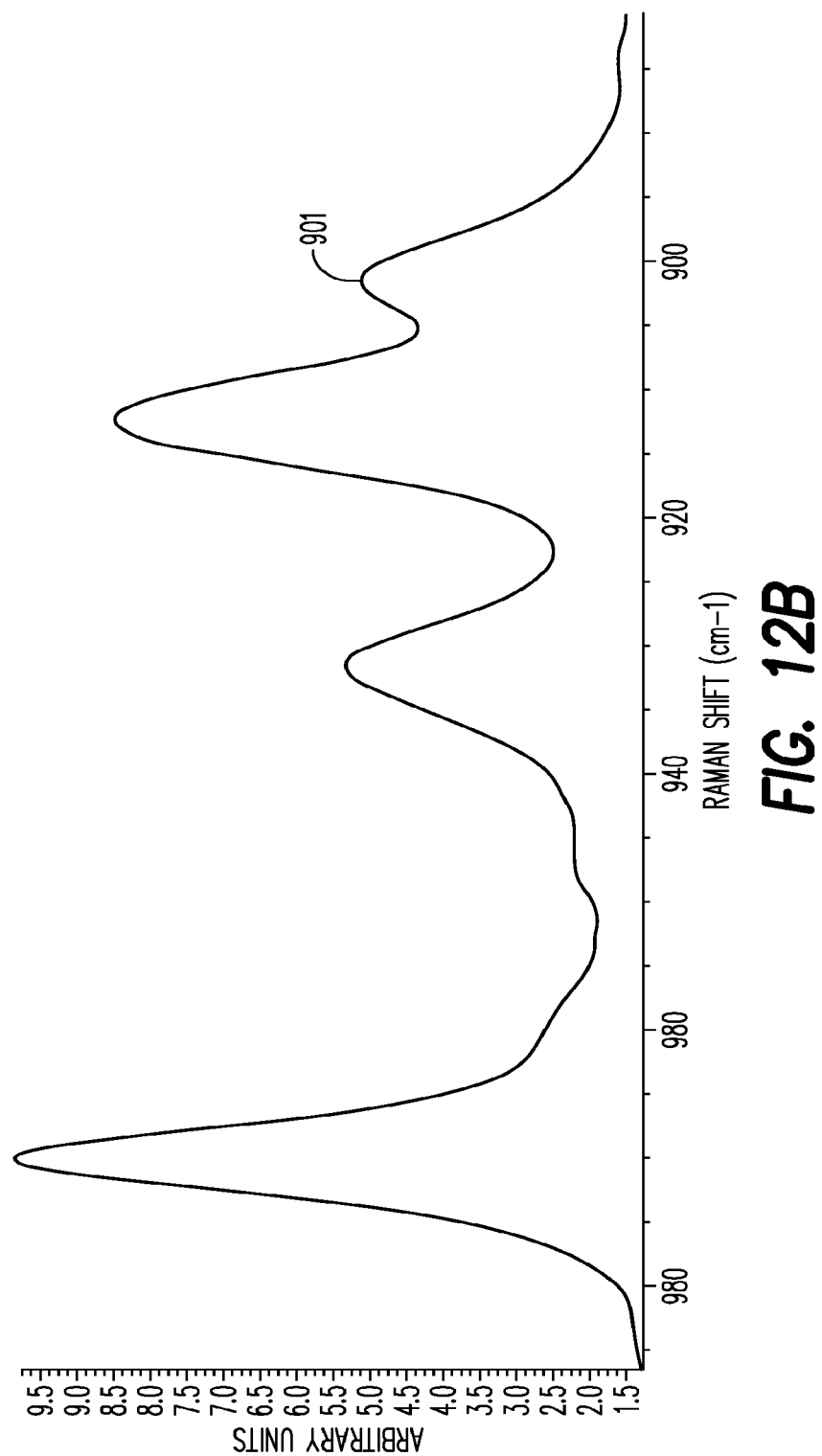

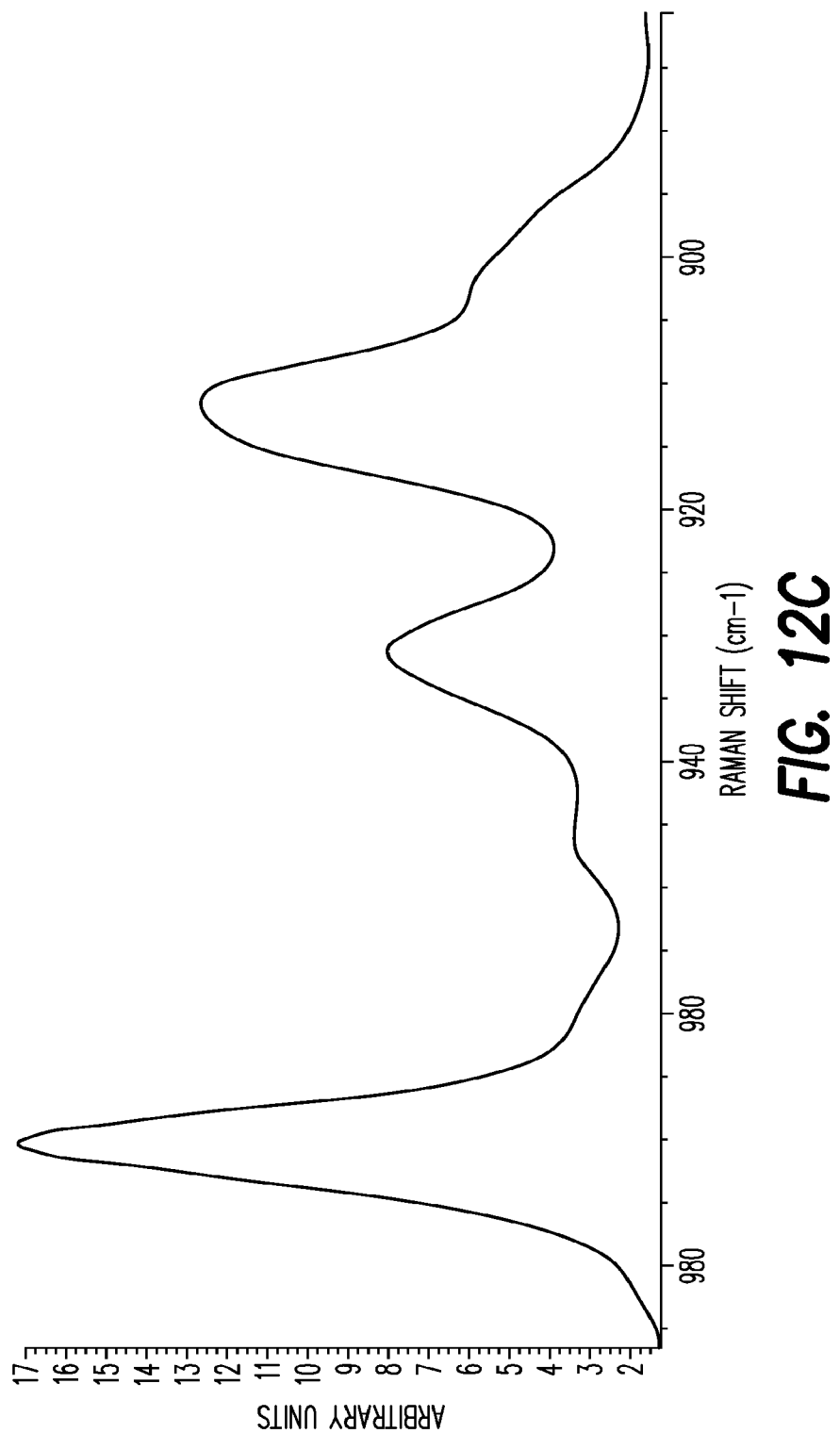

PROCESS OF REWORKING A CRYSTALLINE FORM OF A GLYCINE TRANSPORT INHIBITOR

The present invention concerns reworking of a crystalline compound inhibiting glycine transporter-1 (GlyT1) for the preparation of a pharmaceutical composition, i.e. the invention relates to a process comprising drying the crystalline compound by means of a tray dryer and homogenizing the polymorph in a mixer-dryer.

The invention also relates to the dried and homogenized crystalline substance or compound obtained or obtainable by the process of drying and homogenizing and its use as modulator of GlyT1.

In a further aspect, the present invention relates to a pharmaceutical composition, comprising the dried and homogenized crystalline substance or compound, optionally together with one or more inert carriers and/or diluents. In a more specific embodiment, the present invention relates to pharmaceutical granules and tablets comprising the dried and homogenized crystalline substance or compound.

In one aspect the crystalline substance or compound inhibiting GlyT1 is a crystalline form of [5-(methylsulfonyl)-2-{[(2R)-1,1,1-trifluoropropan-2-yl]oxy}phenyl]{(1R,5R)-1-[5-(trifluoromethyl)-1,2-oxazol-3-yl]-3-azabicyclo[3.1.0]hex-3-yl}methanone ("the Compound"), and its structure is

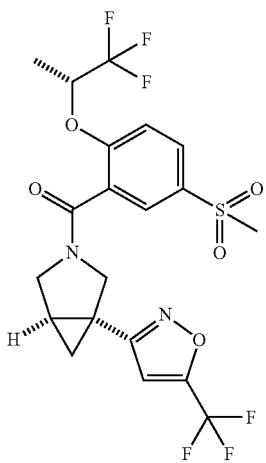 [SMILES: C[C@@H](Oc1ccc(S(C)(=O)=O)cc1C(=O)N1C[C@@H]2C[C@]2(c2cc(C(F)(F)F)on2)C1)C(F)(F)F]

The synthesis of the Compound, which may also be named ([5-Methylsulfonyl-2-((R)-2, 2, 2-trifluoro-1-methyl-ethoxy)-phenyl]-[(1R,5R)-1-(5-trifluoromethyl-isoxazol-3-yl)-3-aza-bicyclo[3.1.0]hex-3-yl]-methanone, is described in WO 2013/017657 and is obtained in amorphous form. Crystalline forms are not disclosed nor mentioned.

The process of the invention described herein concerns reworking (e.g. drying and homogenization) of the Compound after it is obtained from a crystallization process and isolated by centrifugation or filtration ("the crystallization product(s)"). The process allows reworking of the Compound in multi kilogram scale and is suitable to be applied to commercial scale.

WO2020/223419 discloses three polymorphs of the Compound (polymorph I, II and III) and corresponding processes for their manufacture. The disclosed polymorphs obtained according to the processes (polymorphs I, II and III) are suitable crystallization products and as such can be used for the process of reworking disclosed herein.

Accordingly, in one aspect, the crystallization product is a crystalline polymorph of the Compound, e.g. polymorph I, II, or III (or different mixtures thereof) as described in WO2020/223419. The disclosure of WO2020/223419 is herewith incorporated by reference.

In a more specific aspects, the crystallization product is polymorph I or II or mixtures thereof.

Further aspects of the present invention relate to the dried and homogenized crystalline Compound and a pharmaceutical composition comprising the dried and homogenized Compound and its use in the prevention and/or treatment of a neurological or a psychiatric disorder.

Accordingly, a further aspect of the present invention relates to the dried and homogenized polymorph I, II or mixtures thereof or a pharmaceutical composition comprising the dried and homogenized polymorph I, II or mixtures thereof for the use in the prevention and/or treatment of a neurological or a psychiatric disorder.

Yet another aspect of the present invention relates to the dried and homogenized polymorph II of the Compound or a pharmaceutical composition comprising said dried and homogenized polymorph II of the Compound for use in the prevention and/or treatment of diseases or conditions which can be influenced by inhibition of GlyT1, such as conditions concerning positive and negative symptoms of schizophrenia as well as cognitive impairments associated with schizophrenia, and other neurological and psychiatric disorders. The use comprises the manufacture of medicaments for the treatment of the corresponding diseases.

The present invention, thus, discloses a crystalline form of [5-(methylsulfonyl)-2-{[(2R)-1,1,1-trifluoropropan-2-yl]oxy}phenyl]{(1R,5R)-1-[5-(trifluoromethyl)-1,2-oxazol-3-yl]-3-azabicyclo[3.1.0]hex-3-yl}methanone
dried in a tray dryer or a pan dryer and subsequently homogenized.

In a further aspect the crystalline form of the Compound is polymorph II.

Polymorph II of the Compound can be prepared in a form that is substantially free of the other polymorphs, wherein "substantially free" means that the solid Compound contains at least about 75% of crystalline polymorph II based on the total molar amount of the Compound. Preferably the Compound comprises at least 80% of Polymorph II on the total molar amount of the Compound. In another preferred embodiment, the crystalline Compound of the invention comprises at least 90% of polymorph II based on the total molar amount of the compound. In yet another preferred embodiment, the crystalline Compound comprises at least 95% of polymorph II based on the total molar amount of the Compound. The crystalline form of the Compound can also comprise a mixture of different polymorphic forms such as Form I and Form II. If not defined otherwise, it can also comprise combinations of an amorphous form of the Compound and a crystalline polymorph II of the Compound.

Different polymorphic forms of the Compound inhibiting GlyT1 can be characterized by the methods described below.

X-Ray Powder Diffraction (XRPD)

X-ray powder diffraction analyses for samples of the different polymorphs can be conducted on a Bruker AXS X-Ray Powder Diffractometer Model D8 Advance, using CuKa radiation (1.54 A) in parafocusing mode with a graphite monochromator and a scintillation detector. Each pattern is obtained by scanning over a range of 2 degrees-35 degrees 2 T, step size of 0.05 degrees 2 T, step time of 4 sec per step. The values reported in the tables have a standard deviation of ±0.2 2Θ.

Differential Scanning Calorimetry (DSC)

DSC analysis can be performed with a differential scanning calorimeter (Q2000, TA instruments, New Castle, DE), using general procedure, 002-GP-00343. Samples are heated from 25° C. to 200° C. and the thermal events are determined.

Water Sorption

Water sorption isotherms can be determined using a dynamic vapor sorption system (Advantage, DVS, London, UK). The samples are subjected to 0 to 90% relative humidity (RH) stepwise with a step size of 10% at 25° C. Each sample is equilibrated at each RH step for at least 60 min, and equilibrium is assumed if weight increase is less than 0.1% within one minute, and the maximum duration on each RH is 6 hours. Therefore, each sample is held at a given RH for 1 to 6 hours depending on how fast the equilibrium is reached.

Solid-State NMR (SSNMR)

$^{13}$C Solid-state NMR (SSNMR) data for Polymorph II can be acquired on a Bruker Avance III NMR spectrometer (Bruker Biospin, Inc., Billerica, MA) at 9.4 T ($^1$H=400.46 MHz, $^{13}$C=100.70 MHz). Samples are packed in 4 mm outside diameter zirconia rotors with Kel-F® drive tips. A Bruker model 4BL CP BB WVT probe is used for data acquisition and sample spinning about the magic-angle (54.74 degrees). Sample spectrum acquisition uses a spinning rate of 12 kHz. A standard cross-polarization pulse sequence is used with a ramped Hartman-Hahn match pulse on the proton channel at ambient temperature and pressure. The pulse sequence uses a 3-millisecond contact pulse and a 5 second recycle delay. Two-pulse phase modulated (tppm) decoupling is also employed in the pulse sequence. No exponential line broadening is used prior to Fourier transformation of the free induction decay. Chemical shifts are referenced using the secondary standard of adamantane, with the upfield resonance being set to 29.5 ppm. The magic-angle is set using the $^{79}$Br signal from KBr powder at a spinning rate of 5 kHz. Table 2a, 4a and 6 list the chemical shifts obtained from $^{13}$C SSNMR spectra acquired for polymorph I, II and III respectively. The values reported have a standard deviation of ±0.2 ppm.

$^{19}$F Solid-state NMR (SSNMR) data for the polymorphs can be acquired on a Bruker Avance III NMR spectrometer (Bruker Biospin, Inc., Billerica, MA) at 9.4 T ($^1$H=400.46 MHz, $^{19}$F=376.76 MHz). Samples are packed in 3.2 mm outside diameter zirconia rotors with Kel-F® drive tips. A Bruker model 3.2BL BB probe is used for data acquisition and sample spinning about the magic-angle (54.74 degrees). Sample spectra are acquired with a spinning rate of 22 kHz. A standard spin echo pulse sequence is used with a 12 second recycle delay. SPINAL-64 1H decoupling is also employed. No exponential line broadening is used prior to Fourier transformation of the free induction decay. Chemical shifts are referenced using the most intense signal from polyvinylidene fluoride (PVDF), with the resonance being set to −91 ppm. The magic-angle is set using the $^{79}$Br signal from KBr powder at a spinning rate of 5 kHz. Table 2b and 4b include the chemical shifts obtained from $^{19}$F SSNMR spectra acquired for polymorph I and II, respectively. The values reported have a standard deviation of ±0.2 ppm.

Raman Spectra

Raman spectra for samples of the different polymorphs were acquired on a Nicolet 6700 FT-Raman Module AEU0900515 spectrometer. Form II exhibits a Raman scattering peak at 901 l/cm, which is not observed in Forms I and III. The relative intensity of this peak may be used to estimate the relative amount of Form II present in the crystalline forms of the Compound.

Characteristics of Polymorph I (Form I)

The X-ray powder diffraction (XRPD) pattern of Form I of the Compound is listed in Table 1.

Thermal analysis profile of polymorph I can be determined by DSC measurement.

Characteristic XRPD peaks, $^{13}$C solid-state nuclear magnetic resonance peaks, and $^{19}$F solid-state nuclear magnetic resonance peaks for Form I are provided in Table 1, Table 2a, and Table 2b, respectively.

TABLE 1

X-ray powder diffraction (XRPD) characteristics for Form I.

| 2Θ, [°] | Intensity I/I, [%] |
| --- | --- |
| 4.6 | 5 |
| 7.9 | 1 |
| 8.5 | 4 |
| 9.2 | 6 |
| 9.5 | 6 |
| 10.0 | 11 |
| 12.2 | 12 |
| 13.8 | 6 |
| 15.2 | 6 |
| 15.7 | 6 |
| 16.7 | 40 |
| 17.2 | 11 |
| 17.5 | 5 |
| 18.0 | 3 |
| 18.5 | 8 |
| 19.0 | 59 |
| 20.0 | 100 |
| 20.8 | 4 |
| 21.5 | 6 |
| 22.7 | 80 |
| 23.2 | 12 |
| 24.1 | 2 |
| 24.7 | 2 |
| 25.2 | 1 |
| 25.9 | 4 |
| 26.4 | 2 |
| 27.0 | 2 |
| 27.9 | 6 |
| 28.7 | 6 |
| 29.7 | 4 |
| 33.3 | 2 |

TABLE 2a

13C NMR Chemical Shifts for Form I.

| Peak | Chemical Shift (ppm) |
| --- | --- |
| 1 | 167.2 |
| 2 | 166.6 |
| 3 | 165.8 |
| 4 | 165.3 |
| 5 | 160.5 |
| 6 | 159.4 |
| 7 | 158.8 |
| 8 | 158.3 |
| 9 | 156.9 |
| 10 | 134.6 |
| 11 | 132.5 |
| 12 | 132.0 |
| 13 | 131.5 |
| 14 | 130.2 |
| 15 | 129.1 |
| 16 | 128.7 |
| 17 | 127.9 |
| 18 | 127.2 |
| 19 | 126.6 |
| 20 | 126.1 |

TABLE 2a-continued

13C NMR Chemical Shifts for Form I.

| Peak | Chemical Shift (ppm) |
|---|---|
| 21 | 123.3 |
| 22 | 120.4 |
| 23 | 119.4 |
| 24 | 117.4 |
| 25 | 115.4 |
| 26 | 113.8 |
| 27 | 102.4 |
| 28 | 101.6 |
| 29 | 72.0 |
| 30 | 49.0 |
| 31 | 46.8 |
| 32 | 45.7 |
| 33 | 28.7 |
| 34 | 27.7 |
| 35 | 26.9 |
| 36 | 25.7 |
| 37 | 25.1 |
| 38 | 23.6 |
| 39 | 18.8 |
| 40 | 18.4 |
| 41 | 14.0 |
| 42 | 13.7 |

TABLE 2b $^{19}$F NMR Chemical Shifts for Form I.

| Peak | Chemical Shift (ppm) |
|---|---|
| 1 | −64.3 |
| 2 | −64.8 |
| 3 | −65.9 |
| 4 | −66.8 |
| 5 | −78.0 |
| 6 | −78.5 |
| 7 | −79.3 |
| 8 | −80.0 |

In one embodiment of the invention, Form I of the Compound has the XRPD characteristics shown in Table 1.

In another embodiment of the invention, Form I of the Compound is characterized by at least three XRPD peaks at 2Θ angles selected from 4.6°, 10.0°, 16.7° and 18.0°.

In another embodiment of the invention, Form I of the Compound is characterized by XRPD peaks at 2Θ angles selected from 4.6°, 10.0°, 16.7°, 19.0°, 20.0° and 22.7°.

In another embodiment of the invention, Form I of the Compound is characterized by XRPD peaks at 2Θ angles selected from 4.6°, 9.2°, 10.0°, 12.2°, 16.7°, 17.2°, 18.5°, 19.0°, 20.0°, 22.7°.

In yet another embodiment of the invention, Form I of the Compound is characterized by the $^{13}$C solid-state nuclear magnetic resonance peaks shown in Table 2a.

In another embodiment of the invention, Form I of the Compound is characterized by at least three $^{13}$C solid-state nuclear magnetic resonance peaks at chemical shifts selected from 131.5 ppm, 127.2 ppm, 28.7 ppm, and 25.7 ppm.

In another embodiment of the invention, Form I of the Compound is characterized by $^{13}$C solid-state nuclear magnetic resonance peaks at chemical shifts selected from 131.5 ppm, 127.2 ppm, 28.7 ppm, and 25.7 ppm.

In another embodiment of the invention, Form I of the Compound is characterized by $^{13}$C solid-state nuclear magnetic resonance peaks at chemical shifts selected from 167.2 ppm, 159.4 ppm, 156.9 ppm, 131.5 ppm, 115.4 ppm, 127.2 ppm, 46.8 ppm, 45.7 ppm, 28.7 ppm, 25.7 ppm, and 13.7 ppm.

In another embodiment of the invention, Form I of the Compound is characterized by the $^{19}$F solid-state nuclear magnetic resonance characteristics shown in Table 2b.

In another embodiment of the invention, Form I of the Compound is characterized by at least three $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of the Compound is characterized by at least five $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of the Compound is characterized $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of the Compound has the XRPD characteristics shown in Table 1; or the $^{13}$C solid-state nuclear magnetic resonance peaks shown in Table 2a; or the $^{19}$F solid-state nuclear magnetic resonance peaks shown in Table 2b.

In another embodiment of the invention, Form I of the Compound is characterized by at least three XRPD peaks at 2Θ angles selected from 4.6°, 10.0°, 16.7°, and 18.0°; by at least three $^{13}$C solid-state nuclear magnetic resonance peaks at chemical shifts selected from 131.5 ppm, 127.2 ppm, 28.7 ppm, and 25.7 ppm; or by at least three $^{19}$F solid-state nuclear magnetic resonance peaks at chemical shifts selected from −64.3, −64.8, −65.9, −66.8, −78.0, −78.5, −79.3, and −80.0 ppm.

In another embodiment of the invention, Form I of the Compound is characterized by XRPD peaks at 2Θ angles selected from 4.6°, 10.0°, 16.7°, and 18.0°; by $^{13}$C solid-state nuclear magnetic resonance peaks at chemical shifts selected from 131.5 ppm, 127.2 ppm, 28.7 ppm, and 25.7 ppm; or by $^{19}$F solid-state nuclear magnetic resonance peaks at chemical shifts selected from −64.3, −64.8, −65.9, −66.8, −78.0, −78.5, −79.3, and −80.0 ppm.

Characteristics of Polymorph II (Form II)

X-ray powder diffraction (XRPD) characteristics of polymorph II of the Compound are listed in Table 3.

The thermal analysis profile of polymorph II can be determined by DSC measurement.

Characteristic XRPD peaks, $^{13}$C solid-state nuclear magnetic resonance peaks, and $^{19}$F solid-state nuclear magnetic resonance peaks for polymorph II are provided in Table 3, Table 4a, and Table 4b.

TABLE 3

X-ray powder diffraction (XRPD) characteristics of polymorph II.

| 2Θ, [°] | Intensity I/I, [%] |
|---|---|
| 3.3 | 16 |
| 4.1 | 16 |
| 4.6 | 11 |
| 5.8 | 5 |
| 6.9 | 5 |
| 8.1 | 7 |
| 8.6 | 6 |
| 9.2 | 8 |
| 9.5 | 7 |
| 10.0 | 13 |
| 12.2 | 10 |

TABLE 3-continued

X-ray powder diffraction (XRPD) characteristics of polymorph II.

| 2Θ, [°] | Intensity I/I, [%] |
|---|---|
| 13.8 | 7 |
| 15.3 | 16 |
| 15.8 | 19 |
| 16.7 | 36 |
| 16.9 | 37 |
| 17.6 | 8 |
| 18.0 | 27 |
| 18.5 | 18 |
| 19.1 | 61 |
| 20.0 | 100 |
| 20.9 | 25 |
| 21.5 | 12 |
| 22.7 | 70 |
| 23.3 | 25 |
| 24.0 | 9 |
| 24.7 | 13 |
| 25.2 | 9 |
| 25.9 | 8 |
| 26.5 | 10 |
| 27.1 | 9 |
| 27.9 | 11 |
| 28.8 | 12 |
| 29.6 | 10 |
| 30.2 | 7 |
| 32.2 | 7 |
| 33.2 | 8 |

TABLE 4a $^{13}$C NMR Chemical Shifts of polymorph II.

| Peak | Chemical Shift (ppm) |
|---|---|
| 1 | 167.3 |
| 2 | 166.8 |
| 3 | 165.9 |
| 4 | 160.5 |
| 5 | 159.6 |
| 6 | 158.9 |
| 7 | 157.1 |
| 8 | 134.7 |
| 9 | 132.7 |
| 10 | 132.1 |
| 11 | 131.6 |
| 12 | 130.1 |
| 13 | 129.2 |
| 14 | 128.0 |
| 15 | 127.3 |
| 16 | 126.3 |
| 17 | 123.5 |
| 18 | 120.2 |
| 19 | 117.5 |
| 20 | 115.6 |
| 21 | 113.8 |
| 22 | 102.6 |
| 23 | 101.7 |
| 24 | 72.2 |
| 25 | 49.8 |
| 26 | 49.2 |
| 27 | 48.6 |
| 28 | 47.9 |
| 29 | 47.6 |
| 30 | 46.9 |
| 31 | 46.6 |
| 32 | 45.9 |
| 33 | 28.3 |
| 34 | 27.2 |
| 35 | 26.5 |
| 36 | 25.5 |
| 37 | 25.0 |
| 38 | 24.0 |
| 39 | 19.3 |
| 40 | 18.4 |
| 41 | 14.2 |
| 42 | 13.6 |
| 43 | 12.9 |

TABLE 4b $^{19}$F NMR Chemical Shifts of polymorph II.

| Peak | Chemical Shift (ppm) |
|---|---|
| 1 | −64.0 |
| 2 | −65.6 |
| 3 | −66.6 |
| 4 | −78.2 |
| 5 | −79.1 |

In one embodiment of the invention polymorph II of the Compound has the XRPD characteristics shown in Table 3.

In another embodiment of the invention, the polymorph II is characterized by at least three XRPD peaks at 2Θ angles selected from 4.1°, 4.6°, 10.0°, 16.7°, and 18.0°.

In yet another embodiment of the invention, the polymorph II is characterized by at least four XRPD peaks at 2Θ angles selected from 4.1°, 4.6°, 10.0°, 16.7°, and 18.0°.

In a further embodiment of the invention, the polymorph II is characterized by XRPD peaks at 2Θ angles selected from 4.1°, 4.6°, 10.0°, 16.7°, and 18.0°.

In yet another embodiment of the invention, the polymorph II is characterized by XRPD peaks at 2Θ angles selected from 4.1°, 4.6°, 10.0°, 15.8°, 18.0°, 18.5°, 19.1°, 20.0°, 20.9°, 22.7°, and 23.3°.

Polymorph II of the Compound can also be characterized as having the $^{13}$C solid-state nuclear magnetic resonance characteristics shown in Table 4a.

Polymorph II can also be characterized by $^{13}$C solid-state nuclear magnetic resonance peaks at chemical shifts selected from 130.1 ppm, 46.6 ppm, and 25.0 ppm.

In even more detail the polymorph II is characterized by $^{13}$C solid-state nuclear magnetic resonance peaks at chemical shifts selected from 167.3 ppm, 157.1 ppm, 130.1 ppm, 115.6 ppm, 72.2 ppm, 47.9 ppm, 46.6 ppm, 45.9 ppm, 25.0 ppm, and 12.9 ppm.

Polymorph II of the Compound can also be characterized as having the $^{19}$F solid-state nuclear magnetic resonance characteristics shown in Table 4b.

Polymorph II can also be characterized by at least three $^{19}$F solid-state nuclear magnetic resonance peaks at chemical shifts selected from −64.0, −65.6, −66.6, −78.2, and −79.1 ppm.

In even more detail the polymorph II is characterized by $^{19}$F solid-state nuclear magnetic resonance peaks at chemical shifts selected from −64.0, −65.6, −66.6, −78.2, and −79.1 ppm.

Polymorph II of the Compound can also be characterized by
the XRPD characteristics shown in Table 3; or
the $^{13}$C solid-state nuclear magnetic resonance peaks shown in Table 4a; or
the $^{19}$F solid-state nuclear magnetic resonance peaks shown in Table 4b.

Polymorph II of the Compound can also be characterized by
- at least three XRPD peaks at 2Θ angles selected from 4.1°, 4.6°, 10.0°, 16.7°, and 18.0°;
- $^{13}C$ solid-state nuclear magnetic resonance peaks at chemical shifts selected from 130.1 ppm, 46.6 ppm, and 25.0 ppm; or
- at least three $^{19}F$ solid-state nuclear magnetic resonance peaks at chemical shifts selected from −64.0, −65.6, −66.6, −78.2, and −79.1 ppm.

Polymorph II of the Compound can also be characterized by
- at least four XRPD peaks at 2Θ angles selected from 4.1°, 4.6°, 10.0°, 16.7°, and 18.0°;
- $^{13}C$ solid-state nuclear magnetic resonance peaks at chemical shifts selected from 130.1 ppm, 46.6 ppm, and 25.0 ppm; or
- $^{19}F$ solid-state nuclear magnetic resonance peaks at chemical shifts selected from −64.0, −65.6, −66.6, −78.2, and −79.1 ppm.

Polymorph II of the Compound can also be characterized by
- XRPD peaks at 2Θ angles selected from 4.1°, 4.6°, 10.0°, 16.7°, and 18.0°;
- $^{13}C$ solid-state nuclear magnetic resonance peaks at chemical shifts selected from 130.1 ppm, 46.6 ppm, and 25.0 ppm; or
- $^{19}F$ solid-state nuclear magnetic resonance peaks at chemical shifts selected from −64.0, −65.6, −66.6, −78.2, and −79.1 ppm.

Water-uptake of polymorph II of the Compound at 25° C. is about 0.04% when maintained at 90% relative humidity for 6 hours under humid nitrogen purge. (In contrast, the water-uptake of the amorphous form of the Compound at 25° C. is 1.4% when maintained at 90% relative humidity for 6 hours under humid nitrogen purge.)

Characteristics of Polymorph III (Form III)

The X-ray powder diffraction (XRPD) characteristics of polymorph III of the Compound are listed in Table 5.

The thermal analysis profile of Form III was determined by DSC measurement.

Characteristic XRPD peaks and $^{13}C$ solid-state nuclear magnetic resonance peaks for Form III are provided in Table 5 and Table 6, respectively.

TABLE 5

X-ray powder diffraction (XRPD) characteristics of Form III.

| 2Θ, [°] | Intensity I/I, [%] |
|---|---|
| 4.2 | 5 |
| 4.8 | 22 |
| 5.1 | 5 |
| 7.6 | 4 |
| 8.1 | 28 |
| 9.7 | 38 |
| 10.3 | 37 |
| 11.3 | 10 |
| 11.9 | 6 |
| 12.0 | 8 |
| 12.8 | 5 |
| 13.7 | 8 |
| 13.9 | 28 |
| 15.2 | 19 |
| 15.3 | 21 |
| 15.6 | 11 |
| 15.9 | 9 |
| 16.2 | 8 |
| 16.5 | 9 |
| 16.8 | 21 |
| 17.1 | 19 |
| 17.5 | 9 |
| 17.9 | 11 |
| 18.2 | 13 |
| 18.4 | 13 |
| 19.0 | 28 |
| 19.3 | 34 |
| 19.6 | 100 |
| 19.9 | 30 |
| 21.0 | 9 |
| 21.4 | 11 |
| 21.6 | 10 |
| 21.8 | 5 |
| 22.1 | 8 |
| 22.6 | 12 |
| 22.8 | 14 |
| 23.3 | 91 |
| 23.6 | 8 |
| 24.2 | 15 |
| 24.6 | 50 |
| 25.7 | 9 |
| 26.5 | 6 |
| 27.5 | 6 |
| 28.1 | 14 |
| 28.6 | 8 |
| 29.4 | 8 |
| 30.0 | 5 |
| 31.0 | 6 |
| 32.1 | 5 |
| 33.3 | 5 |
| 34.2 | 4 |

TABLE 6

$^{13}C$ NMR Chemical Shifts of Form III.

| Peak | Chemical Shift (ppm) |
|---|---|
| 1 | 168.4 |
| 2 | 167.6 |
| 3 | 166.6 |
| 4 | 166.1 |
| 5 | 160.5 |
| 6 | 157.8 |
| 7 | 156.6 |
| 8 | 156.0 |
| 9 | 134.2 |
| 10 | 132.5 |
| 11 | 129.8 |
| 12 | 128.7 |
| 13 | 127.4 |
| 14 | 127.0 |
| 15 | 125.9 |
| 16 | 114.7 |
| 17 | 113.5 |
| 18 | 103.4 |
| 19 | 101.8 |
| 20 | 71.9 |
| 21 | 70.5 |
| 22 | 48.7 |
| 23 | 48.3 |
| 24 | 47.6 |
| 25 | 46.0 |
| 26 | 44.6 |
| 27 | 28.5 |
| 28 | 27.9 |
| 29 | 25.5 |
| 30 | 25.1 |
| 31 | 19.4 |
| 32 | 18.5 |

TABLE 6-continued $^{13}$C NMR Chemical Shifts of Form III.

| Peak | Chemical Shift (ppm) |
|---|---|
| 33 | 14.3 |
| 34 | 13.0 |

In another embodiment of the invention, Form III of the Compound has the XRPD characteristics shown in Table 5.

In another embodiment of the invention, Form III is characterized by at least three XRPD peaks at 2Θ angles selected from 4.8°, 9.7°, 10.3°, 13.9°, and 24.6°.

In another embodiment of the invention, Form III is characterized by at least four XRPD peaks at 2Θ angles selected from 4.8°, 9.7°, 10.3°, 13.9°, and 24.6°.

In another embodiment of the invention, Form III is characterized by XRPD peaks at 2θ angles selected from 4.8°, 9.7°, 10.3°, 13.9°, and 24.6°.

In another embodiment of the invention, Form III is characterized by XRPD peaks at 2θ angles selected from 4.8°, 8.1°, 9.7°, 10.3°, 13.9°, 19.3°, 19.6°, 23.3°, and 24.6°.

In another embodiment of the invention, Form III has the $^{13}$C solid-state nuclear magnetic resonance characteristics shown in Table 6.

In another embodiment of the invention, Form III is characterized by at least two $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by at least three $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by $^{13}$C solid-state nuclear magnetic resonance peaks at chemical shifts selected from 156.6 ppm, 156.0 ppm, 134.2 ppm, 132.5 ppm, 47.6 ppm, 46.0 ppm, 44.6 ppm, 25.5 ppm, 14.3 ppm, and 13.0 ppm.

In another embodiment of the invention, Form III is characterized by at least three XRPD peaks at 2Θ angles selected from 4.8°, 9.7°, 10.3°, 13.9°, and 24.6°; or at least three $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by at least four XRPD peaks at 2Θ angles selected from 4.8°, 9.7°, 10.3°, 13.9°, and 24.6°; or at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by XRPD peaks at 2θ angles selected from 4.8°, 9.7°, 10.3°, 13.9°, and 24.6°; or at least four $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III is characterized by XRPD peaks at 2θ angles selected from 4.8°, 9.7°, 10.3°, 13.9°, and 24.6°; or $^{13}$C solid-state nuclear magnetic resonance peaks at chemical shifts selected from 156.6 ppm, 134.2 ppm, 46.0 ppm, 25.5 ppm, and 14.3 ppm.

In another embodiment of the invention, Form III has the XRPD characteristics shown in Table 5 or the $^{13}$C solid-state nuclear magnetic resonance peaks shown in Table 6.

Methods of Preparation of Solid Forms of the Compound

Various solid forms including polymorph I, II, III and mixtures of the different polymorphs may be obtained by dissolving the Compound in a suitable solvent ("the dissolution step"), preferably at a temperature above room temperature, e.g., 25° C., more preferably from about 45° C. to about 80° C. The heated solution can then be cooled ("the cooling step") to provide a solid/liquid comprising a solid form such as polymorph I, II or III or a mixture of various solid forms. The heated solutions may be filtered prior to cooling or may be concentrated prior to or during the cooling step ("the concentration step"). The heated solutions may be also be treated with a cosolvent ("the cosolvent treatment step") and it is possible that the cosolvent (when used) is added during the cooling step. The cooling step comprises a stepwise cooling ramp, and a seed crystal or seed slurry ("the seeding step") can be added during the cooling step. Any combinations of the above—may be used to obtain various solid forms including polymorph I, II, III and mixtures thereof. Once cooled, the resulting solids can be collected, washed with a suitable solvent, and dried to provide the various solid forms including polymorph I, II, III or mixtures thereof.

Methods of Making a Mixture of Form I and Form II

In one embodiment, the invention relates to a method of making a mixture of polymorph II and another solid form (Form I) of the Compound, comprising:
  (a) heating a mixture of solid forms or an amorphous form of the Compound in 2-propanol to 70° C. to provide a solution;
  (b) treating the solution obtained in step (a) with water while maintaining a temperature of from 50° C. to 70° C.;
  (c) cooling the aqueous mixture of step (b) to 20° C.; and
  (d) collecting the resulting solids as a mixture of Form I and polymorph II of the Compound.

Methods of Making Form I

Form I of the Compound can be obtained with a method comprising:
  (a) heating the Compound and tert-butyl methyl ether (TBME) or water at 50° to provide a slurry;
  (b) cooling the slurry of step (a); and
  (c) collecting the resulting solids as Form I of the Compound.

In one embodiment, an amorphous form of the Compound is used in step (a) in the embodiment immediately above.

Another embodiment relates to the two embodiments described immediately above but further comprises concentrating the slurry of step (b) prior to cooling the slurry.

Methods of Making Form II

Polymorph II of the Compound can be obtained with a method comprising:
  (a) heating a mixture of the compound and 2-propanol to 70° to provide a solution;
  (b) filtering the solution of step (a);
  (c) cooling the filtrate from step (b) to 55° C.;
  (d) treating the cooled solution of step (c) with water;
  (e) cooling the water-treated mixture of step (d) to 20° C.; and
  (f) collecting the resulting solids as polymorph II of the Compound.

In another method, the method described immediately above, further comprises seeding the water-treated solution of step (d); further mixing the seeded solution at 55° C.; and treating the seeded solution with water before cooling to 20° C.

In either of the two embodiments described immediately above an amorphous form of the Compound or a mixture of its polymorph II with another solid form thereof can be used in step (a).

Another method of making polymorph II of the Compound, comprises:
(a) heating an amorphous form or a mixture of the Compound (a mixture of Form I and polymorph II), 2-propanol and water to 55-60° C. to provide a solution;
(b) filtering the solution of step (a);
(c) heating the filtrate of step (b) to 68-70° C.;
(d) treating the filtrate from step (c) with water while maintaining a temperature of 68-70° C.;
(e) cooling the water-treated filtrate from step (d) to 62-66° C.;
(f) seeding the water-treated solution of step (d) with a seeding slurry comprising Form II of the Compound, water and isopropanol to provide a seeded mixture;
(g) cooling the seeded mixture of step (f) to 55° C.
(h) mixing the seeded solution of step (e) at 55° C.;
(i) treating the seeded solution of step (h) with water to provide a mixture;
(j) cooling the mixture of step (i) to 55° C.;
(k) cooling the cooled-mixture of step (j) to 20° C.; and
(l) collecting the resulting solids as polymorph II of the Compound.

Methods of Making Form III

Form III of the Compound can be obtained with a method comprising:
(a) heating a mixture of the Compound (Form II) and methanol to 50-55° C. to provide a solution;
(b) concentrating the solution of step (a) at 40-45° C.;
(c) cooling the concentrated solution from step (b) to 25° C.; and
(d) collecting the resulting solids as Form III of the Compound.

Another embodiment is identical to the embodiment described immediately above with the exception that Form I of the Compound is used in step (a).

BRIEF DESCRIPTION OF THE FIGURES

FIG. 7A is a $^{13}C$ solid-state NMR spectrum of Form II of the Compound.

FIG. 12B is a Raman spectrum of Form II of the Compound.

FIG. 12C is a Raman spectrum of Form III of the Compound.

FURTHER ASPECTS

Figure 1:
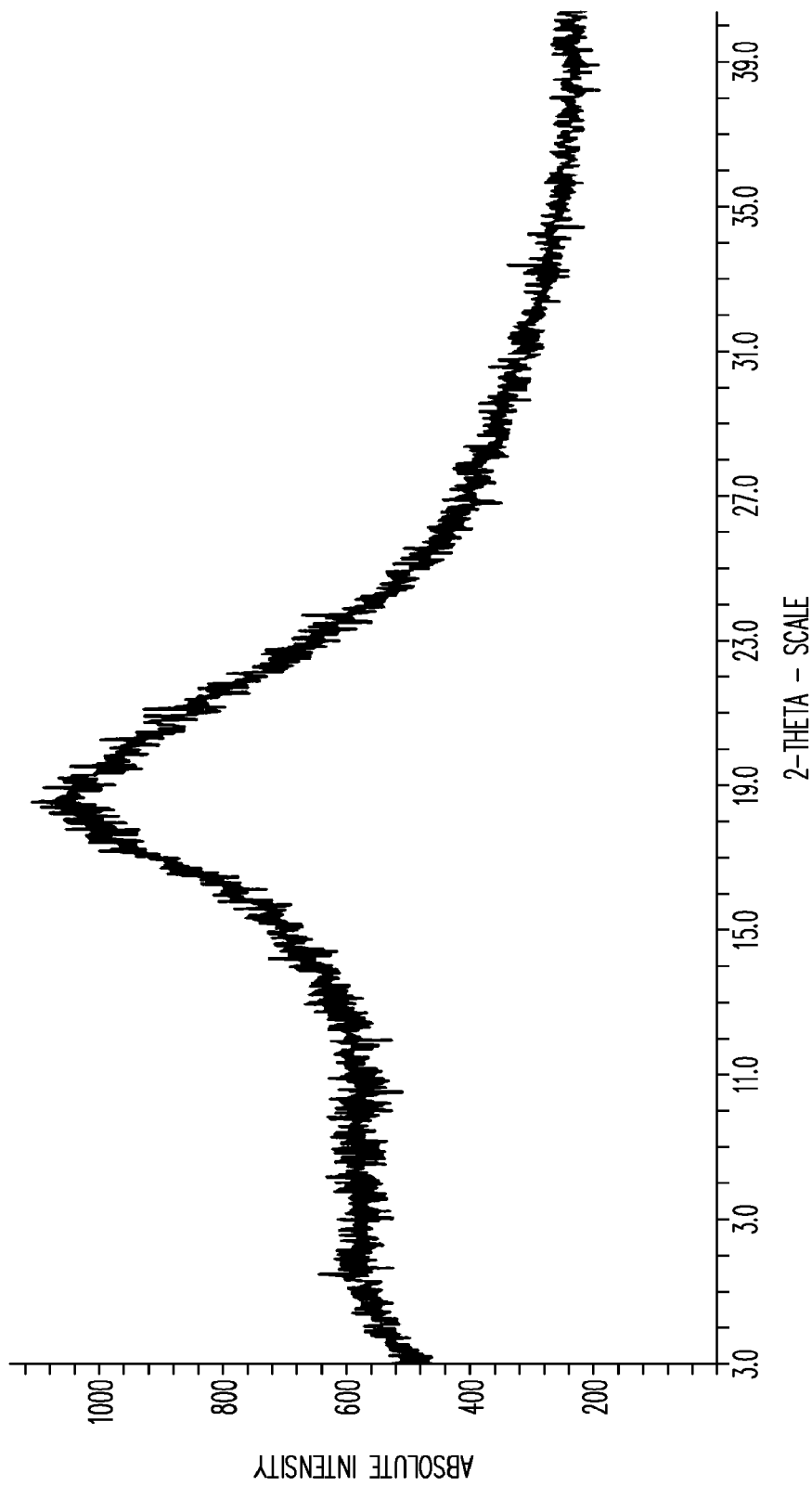
FIG. 1 shows an XRPD pattern of the Compound (amorphous form) prepared according to the procedure of WO2013017657.
Figure 2:
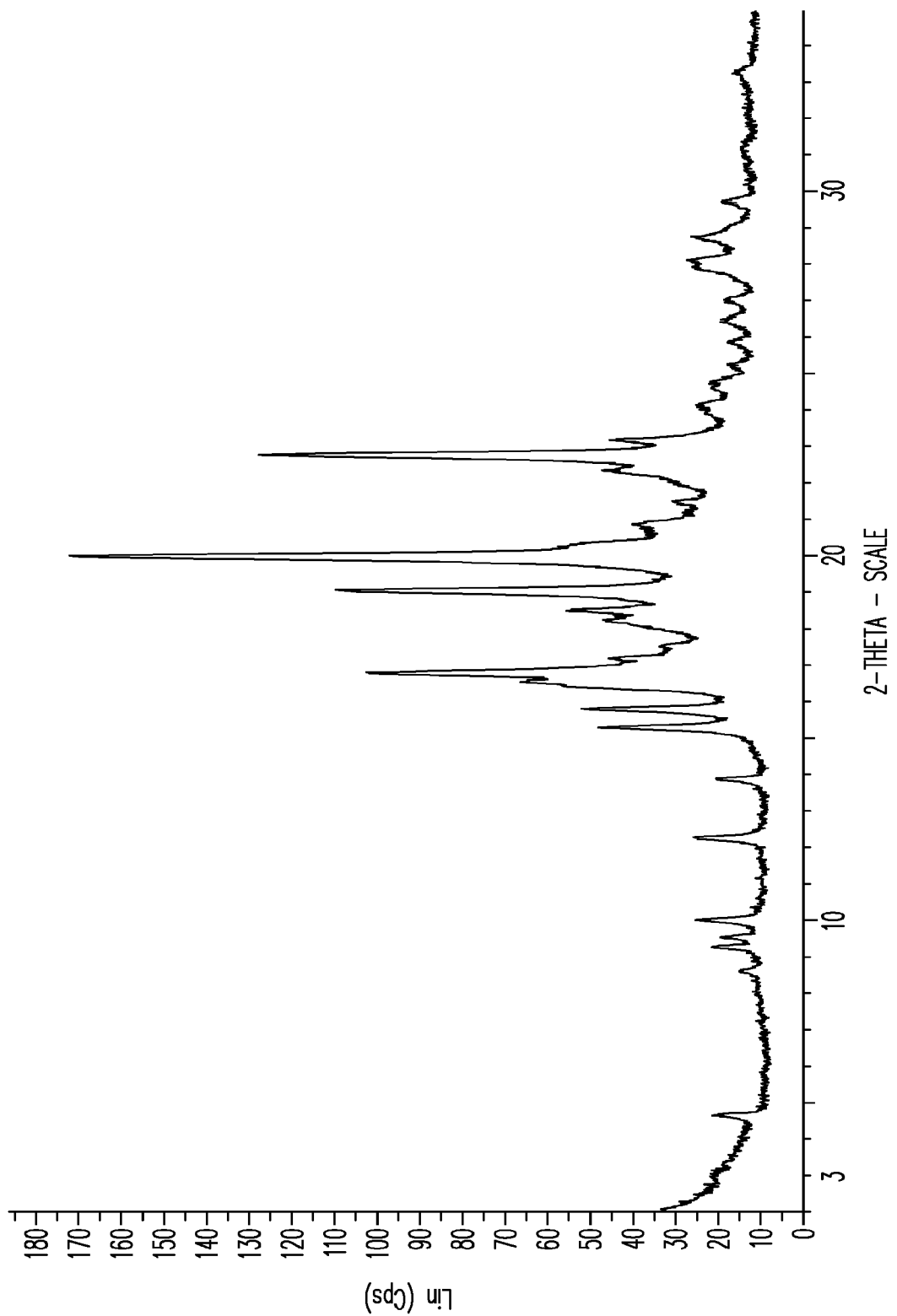
FIG. 2 shows an X-ray powder diffraction (XRPD) pattern of Form I of the Compound.
Figure 3:
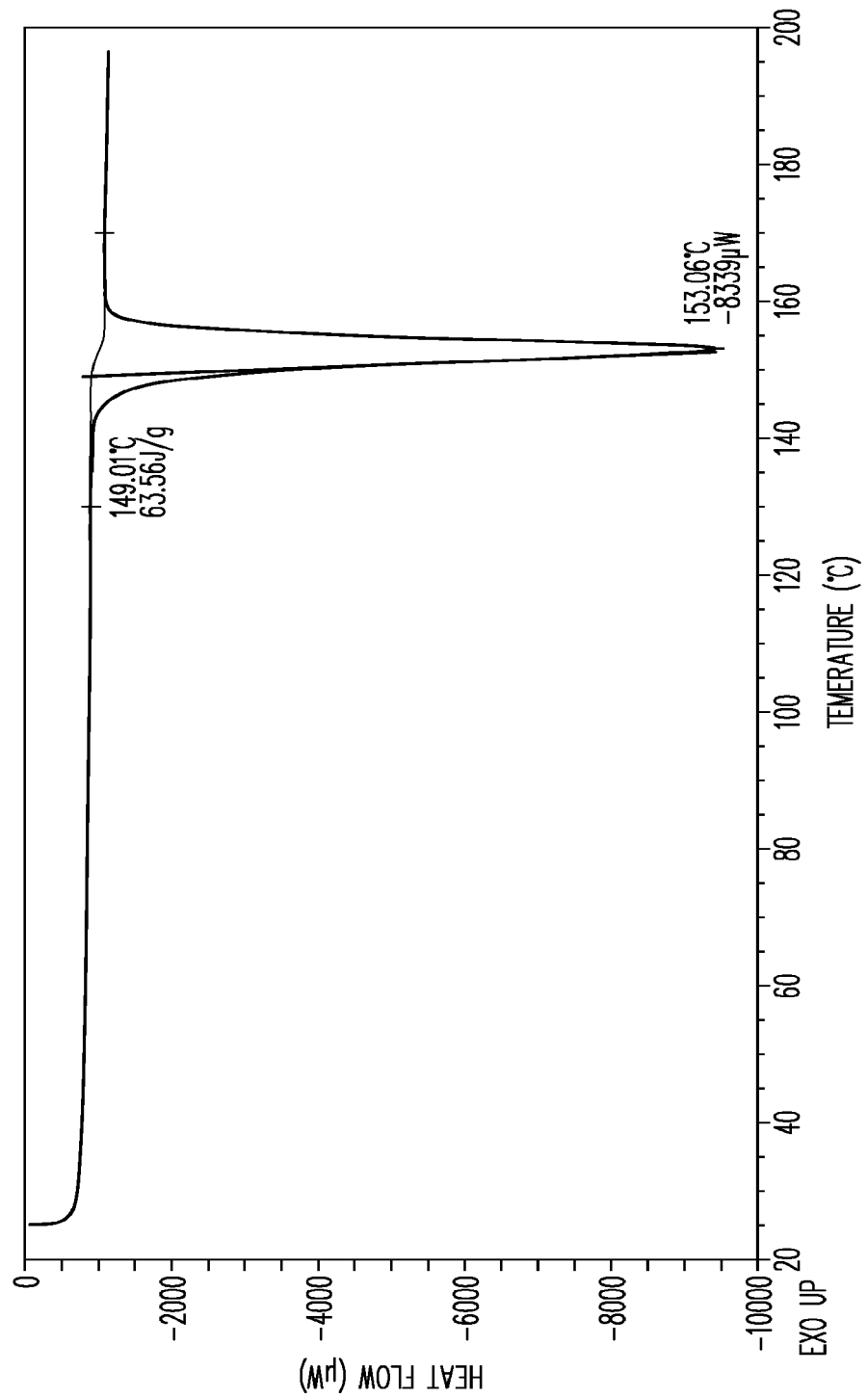
FIG. 3 is a thermal analysis profile of Form I of the Compound determined by DSC measurement.
Figure 4A:
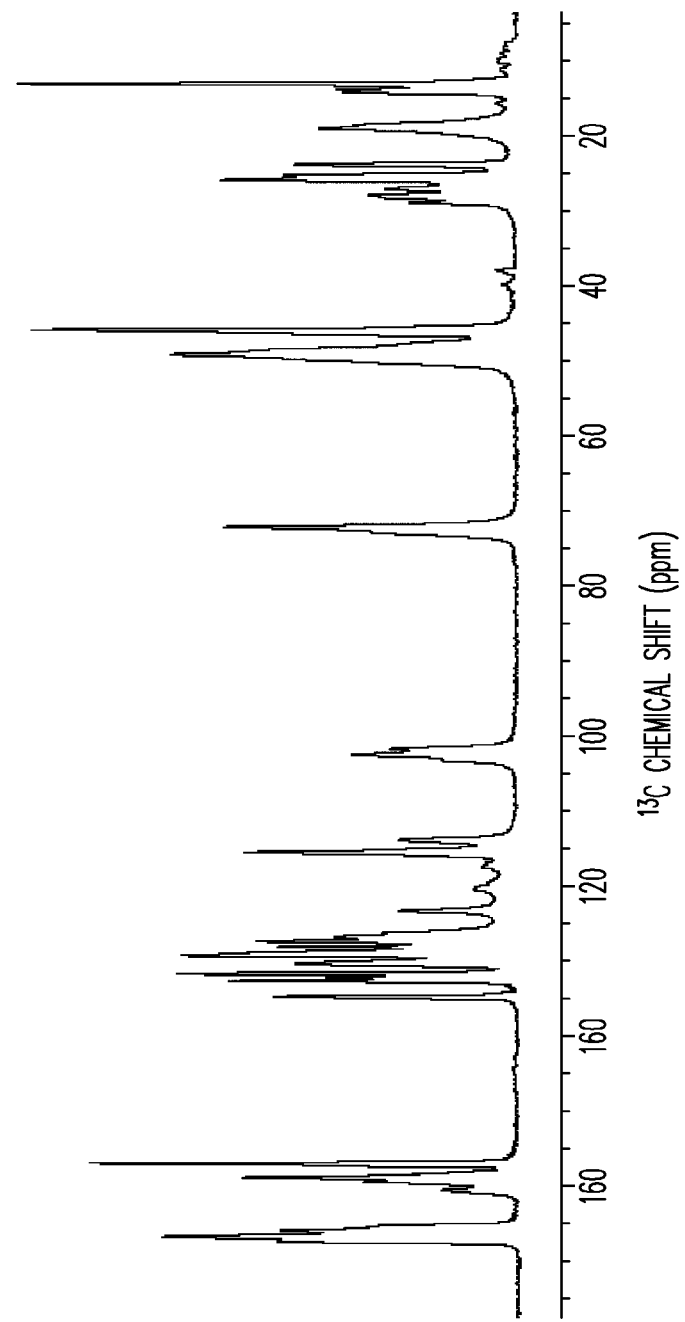
FIG. 4A is a $^{13}C$ solid-state NMR spectrum of Form I of the Compound.
Figure 4B:
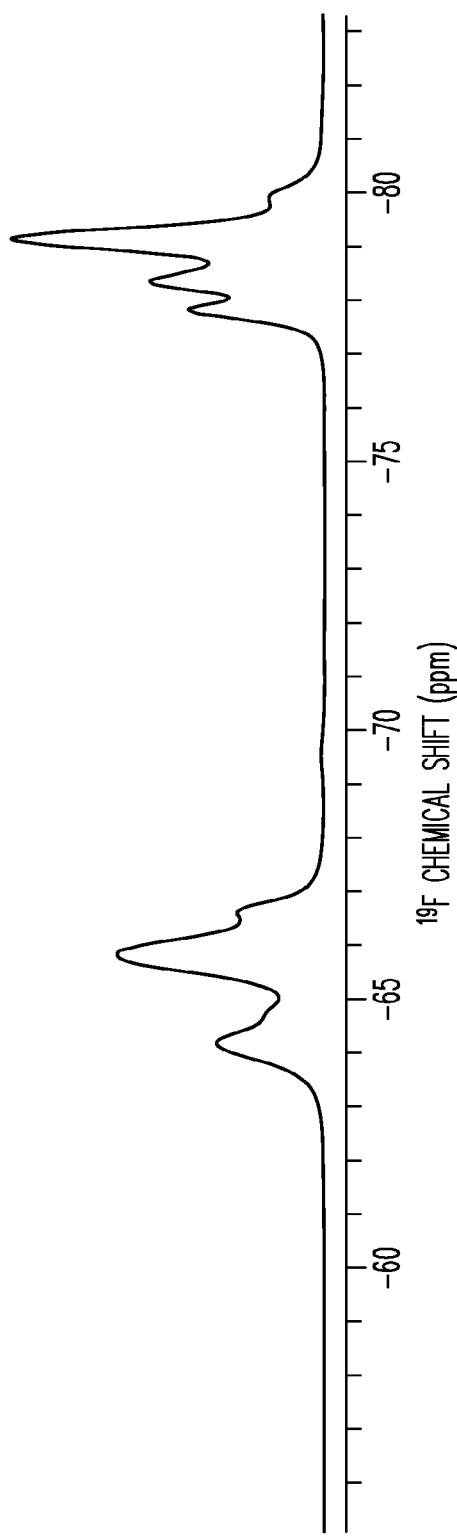
FIG. 4B is a $^{19}F$ solid-state NMR spectrum of Form I of the Compound.
Figure 5:
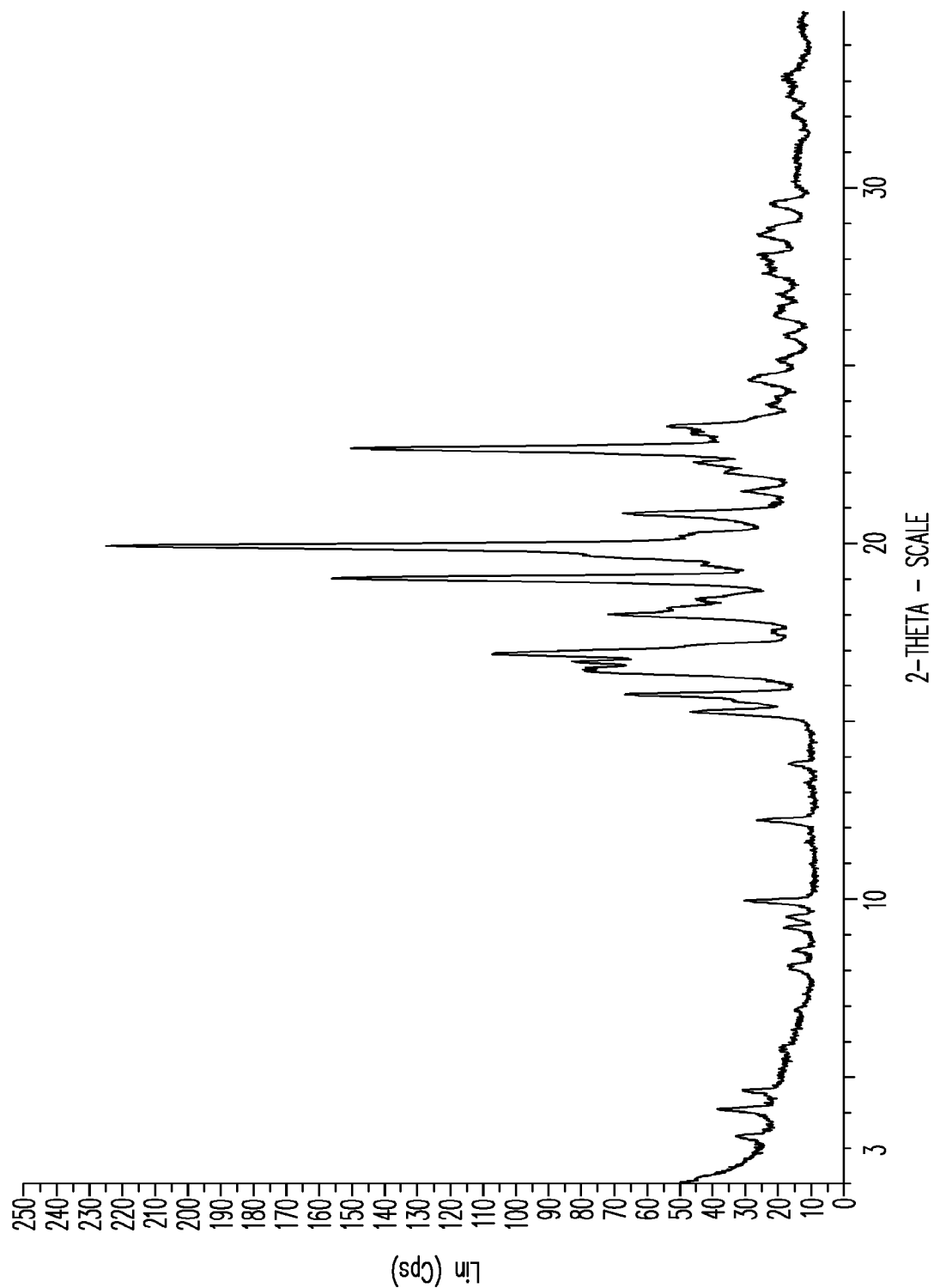
FIG. 5 shows an XRPD pattern of Form II of the Compound.
Figure 6:
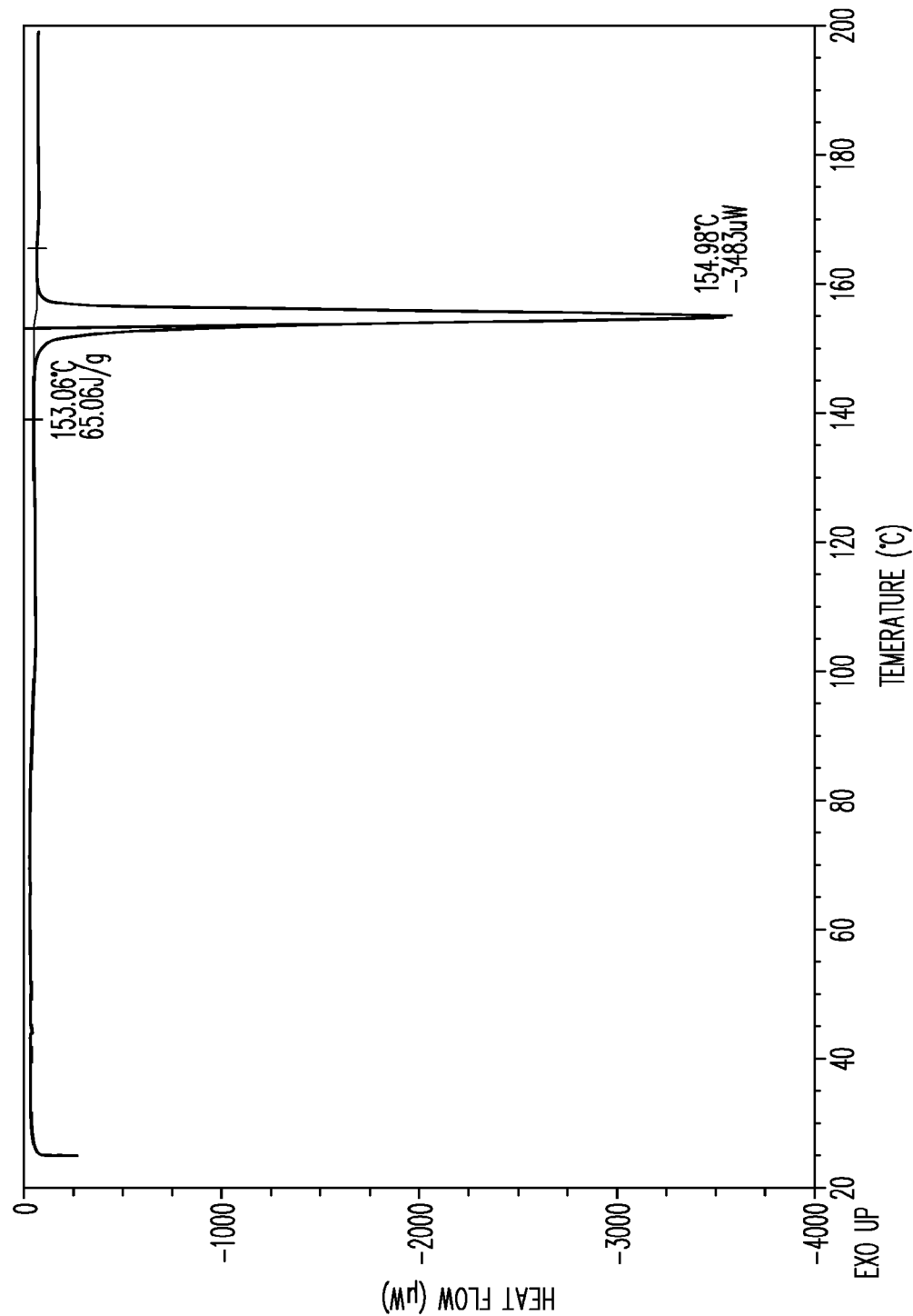
FIG. 6 is a thermal analysis profile of Form II of the Compound determined by DSC measurement.
Figure 7B:
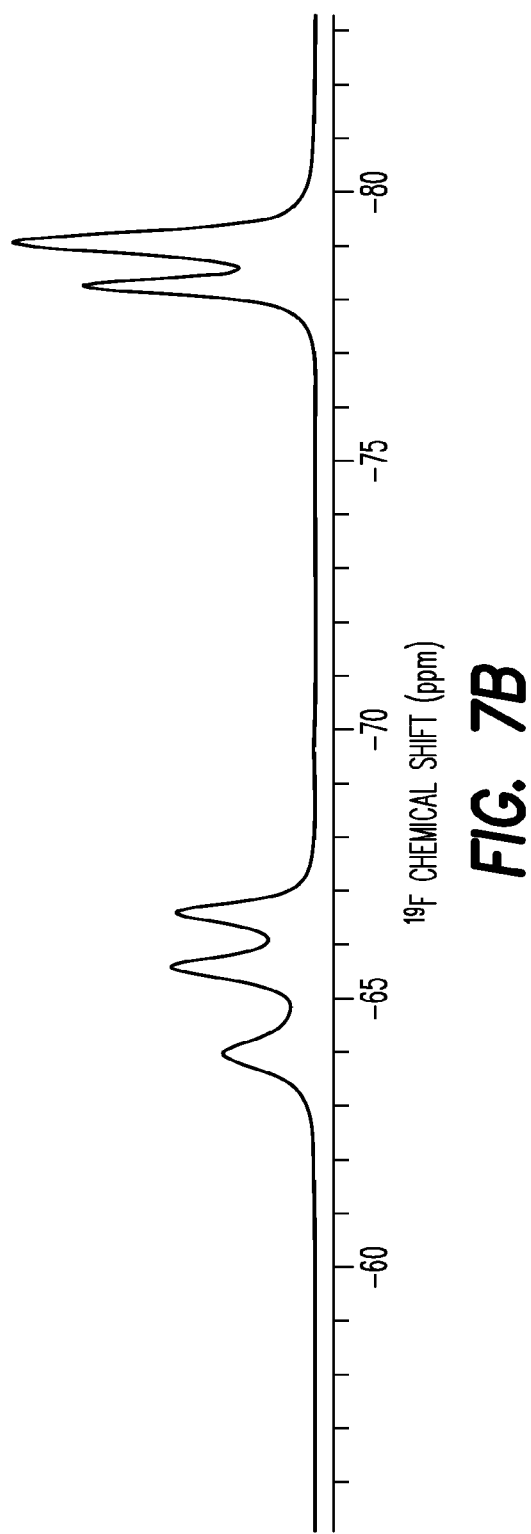
FIG. 7B is a $^{19}F$ solid-state NMR spectrum of Form II of the Compound.
Figure 8:
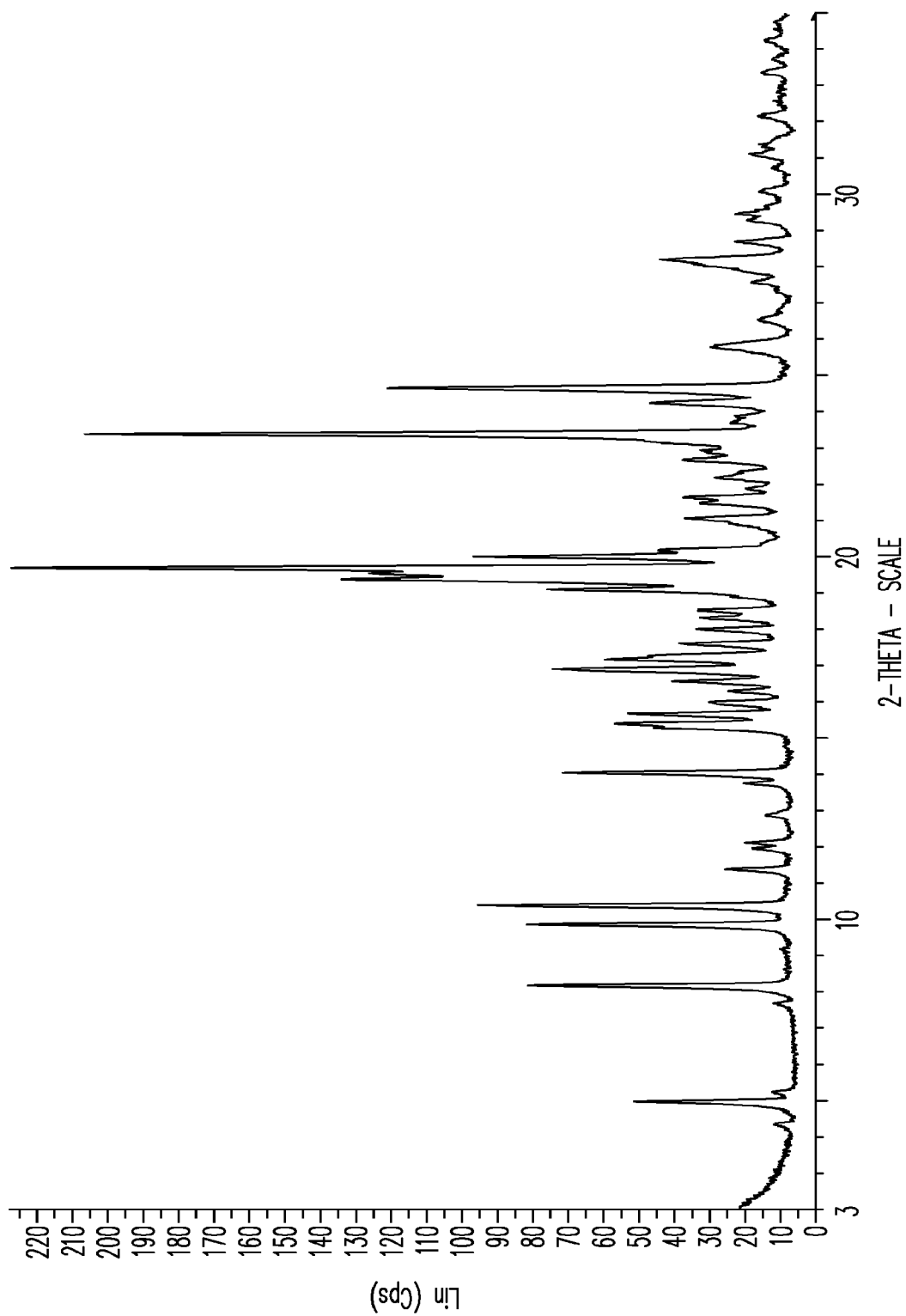
FIG. 8 shows an XRPD pattern of Form III of the Compound.
Figure 9:
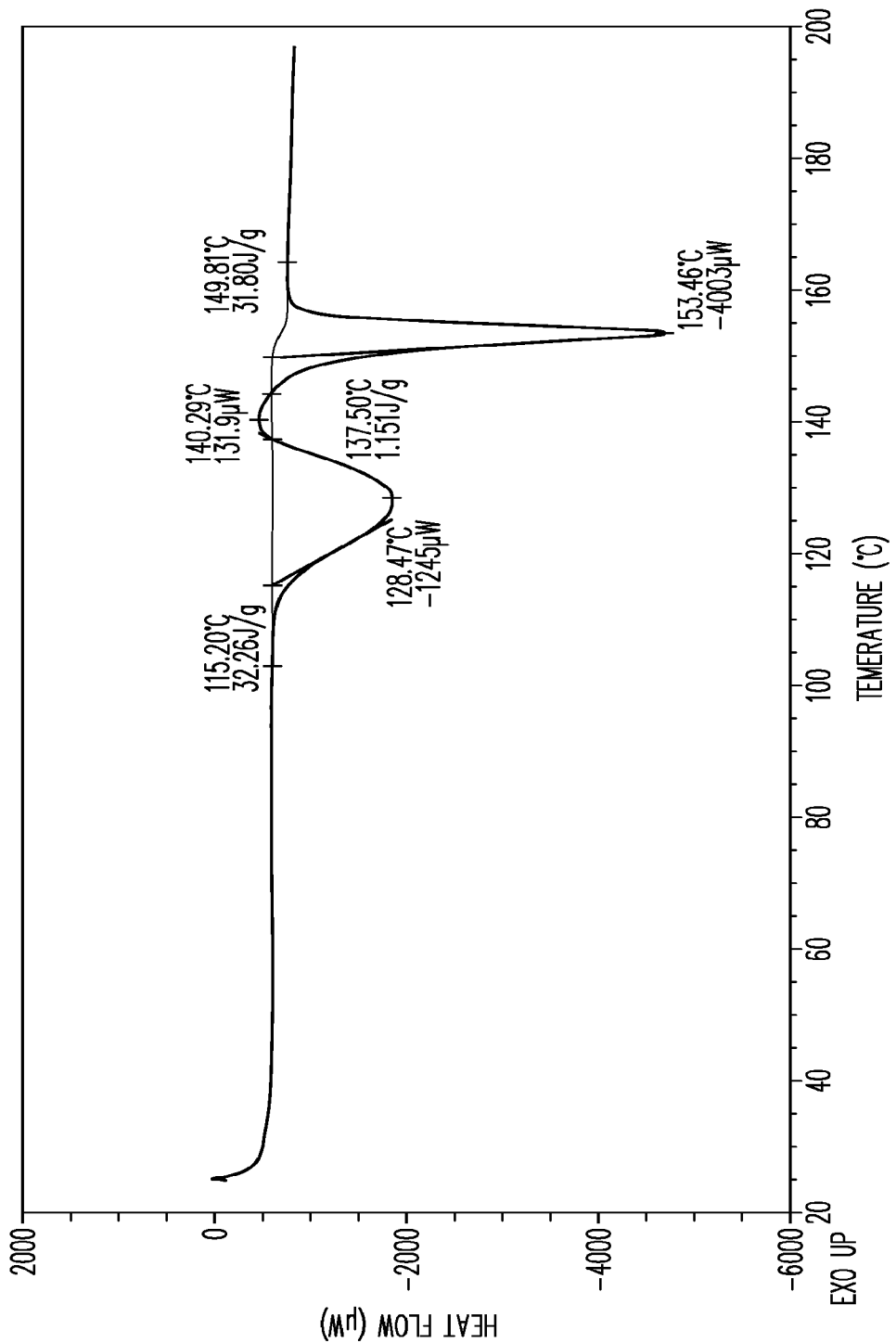
FIG. 9 is a thermal analysis profile of Form III of the Compound determined by DSC measurement.
Figure 10:
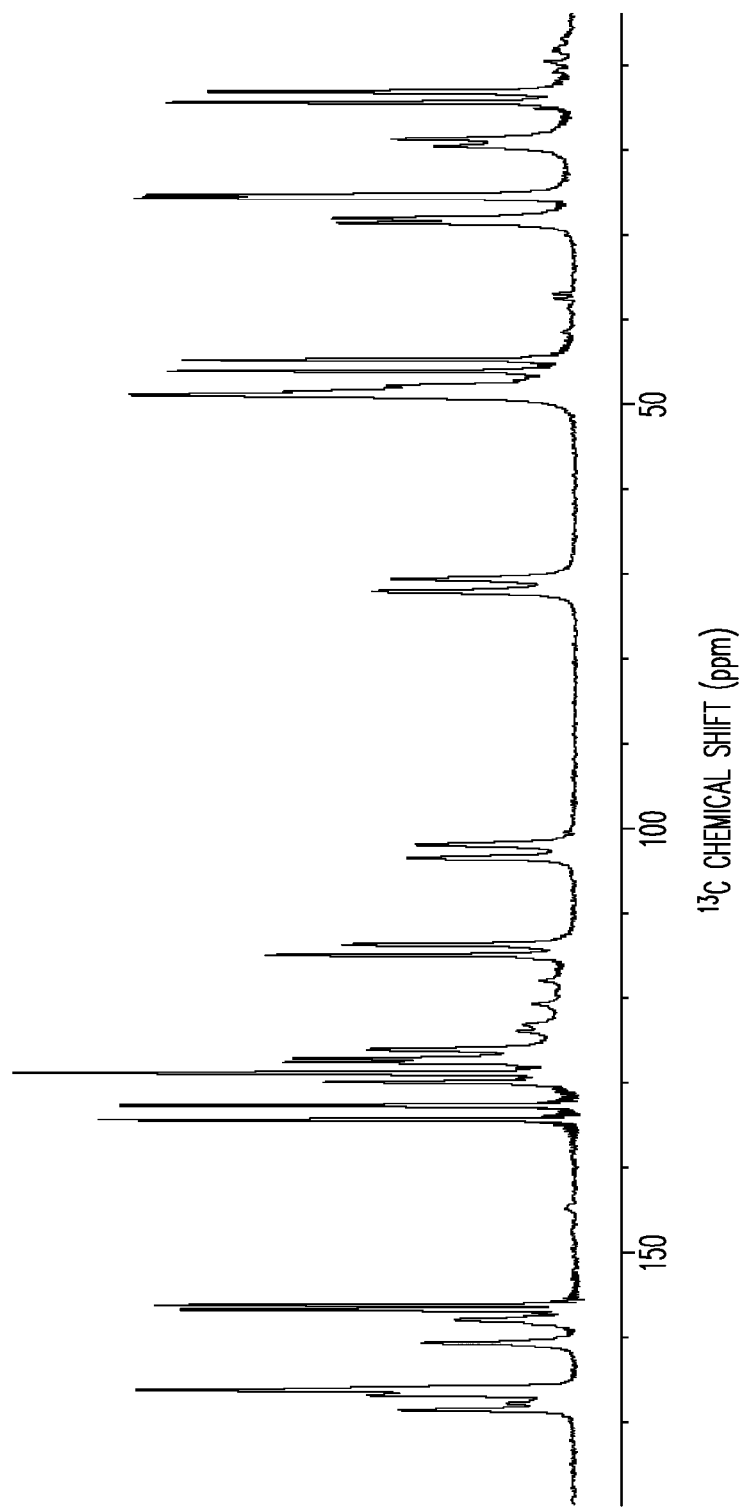
FIG. 10 is a $^{13}C$ solid-state NMR spectrum of Form III of the Compound.
Figure 11:
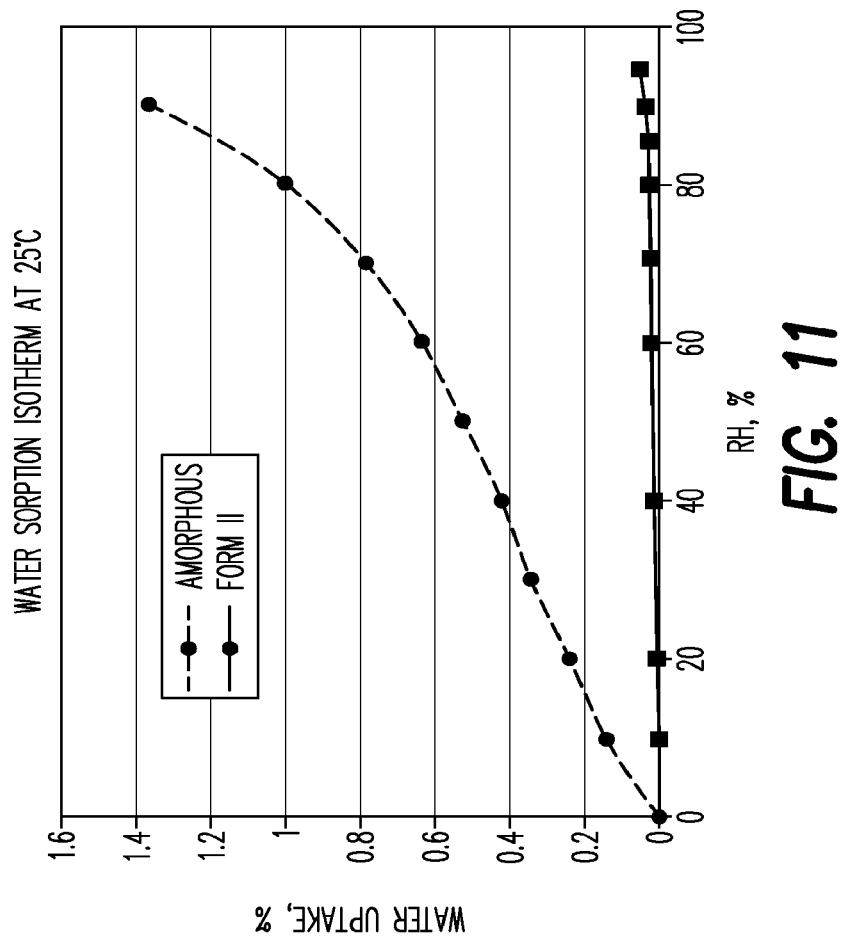
FIG. 11 is a water sorption isotherm showing the water-uptake of Form II of the Compound and amorphous Compound when stored at 25° C. at different relative humidity.
Figure 12A:
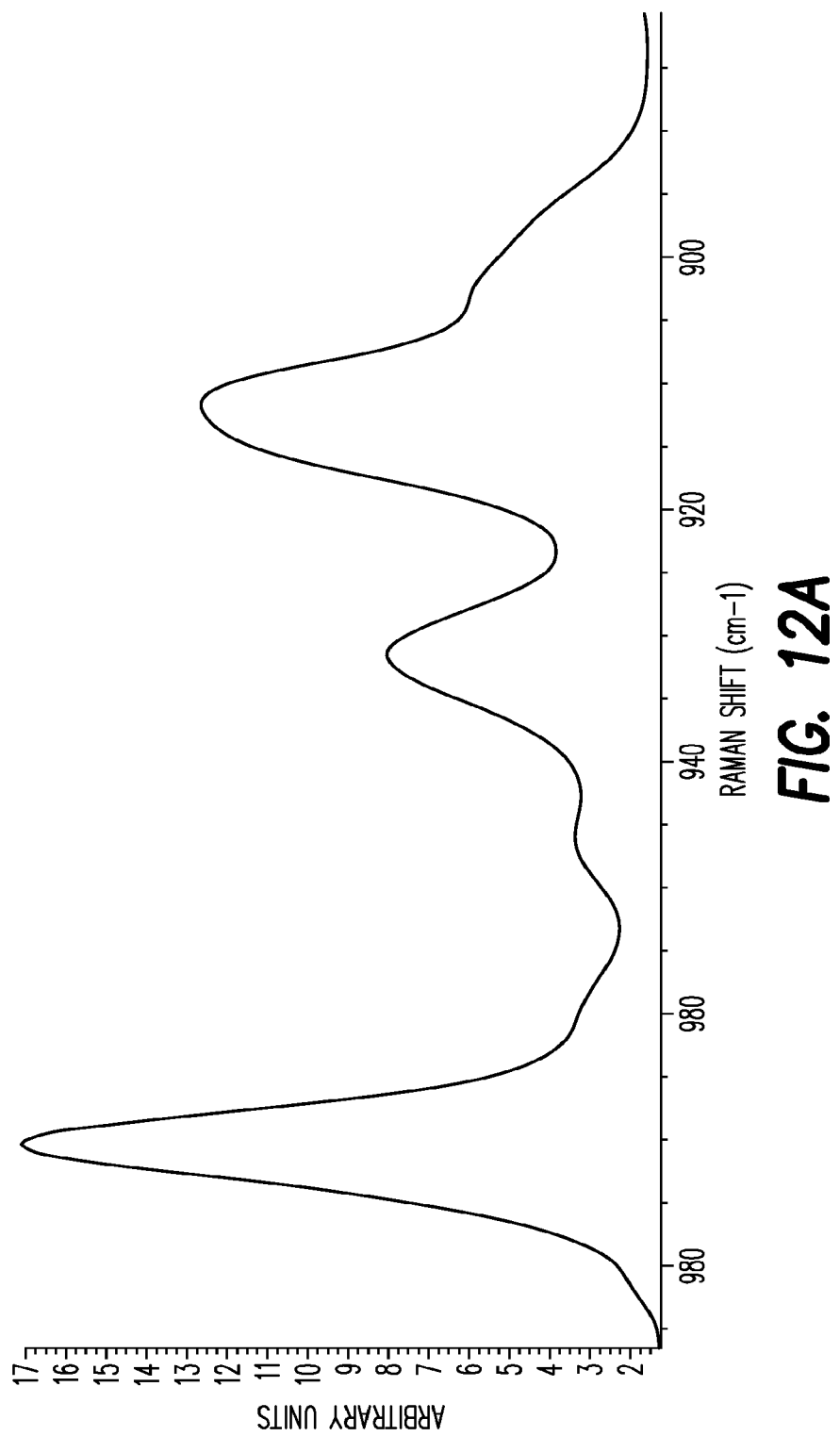
FIG. 12A is a Raman spectrum of Form I of the Compound.

As mentioned above, the core aspect of the present invention is a crystalline form of the Compound dried by means of a tray dryer or a pan dryer and subsequently homogenized.

In order to dry and homogenize the crystalline forms, which may be obtained by above described procedures, a person skilled in the art may choose from various drying options and corresponding equipment, such as universal dryer, mixer-dryer, pan dryer, conical dryer, tray dryer, rotary cone dryer or filter dryer.

A universal dryer is a horizontal vacuum-dryer with a two-armed paddle. On one of the two paddles there is a chopper shaft.

Drying processes in a universal dryer did not turn out robust. The quality of the dried and homogenized product obtained by means of a universal dryer varied (see Examples 5 and 6), and the dissolution behavior of tablets containing the reworked product showed high variability (see dissolution measurements of Example 9 and Table 11).

As can be taken from Example 5 (e.g. batches 17101 and 17102) the drying process in a universal dryer results in changes in the crystalline structure of the Compound and to conversion to amorphous forms. Such conversions lead to increased particle sizes due to agglomeration and finally to clumping.

High quality criteria exist for a pharmaceutical formulation, and usually the same crystalline morphology needs to be guaranteed, since different morphologies may have different dissolution rates, which in turn leads to altered pharmacokinetic properties and potentially to different bioavailability.

Despite investigations into improved reworking conditions using a universal dryer (see Example 6, Table 8), identification of crucial process parameters, whose control would allow for a highly reproducible process providing for a constant dissolution rate (Example 9, Table 10), remains elusive.

However, it has surprisingly been found that drying on trays in a tray dryer under vacuum and subsequent homogenization (Example 7) is robust and yields product of consistent quality with respect to crystallinity and dissolution rate of tablets produced with the reworked Compound (Example 9, Table 10).

Tablets prepared with the crystalline form of the Compound reworked according to the invention (see e.g. Example 8) consistently show a high dissolution rate. Accordingly, tablets prepared from the reworked Compound according to the invention consistently show a dissolution (DP-dissolution) after 45 minutes of more than 80%, e.g. more than 85%, preferably more than 90%, e.g. between 90% to 99% or 95% to 99%.

Without wishing to be bound to any theory, it might be important that the Compound is reworked while minimizing mechanical stress in order to produce drug substance and consequently drug product that shows desired dissolution properties. Drying and or homogenization methods that exert only limited mechanical stress to the Compound might be preferred. However, as mentioned above, improved reworking conditions using a universal dryer (Example 6, Table 8) effecting reduced mechanical stress (e.g. reduced stirring and chopping) did not lead to uniform results in the dissolution experiment (Example 9, Table 10).

Preferred drying equipment is a tray dryer or a pan dryer. In a more specific embodiment the drying equipment is a tray dryer.

Under a tray the person skilled in the art understands a slide-in sheet of metal as a large storage rack in shelves, shelf carts or tray carts, respectively, and drying cabinets.

Suitable dryers are dryers the mantle temperature of which can be predefined between 40° C. and 80° C. Preferred is a mantle temperature of 80° C. or less, e.g. between 50-80° C., or 50-70° C. Particularly preferred is a mantle temperature of 60-70° C.

Drying can be accomplished in the presence of a carrier gas. A suitable carrier gas is argon, neon, nitrogen or xenon. A preferred carrier gas is argon or nitrogen. Particularly preferred is nitrogen.

In another aspect, dryers that can be operated under reduced pressure (vacuum dryers) might be preferred. Accordingly, a vacuum tray dryer or a vacuum pan dryer is preferred. In a more specific aspect, the dryer is a vacuum tray dryer.

Drying is terminated, if in a halogen moisture analyzer (halogen dryer) a loss of drying ≤0.5% is ascertained in a sample at 110° C. The duration of drying amounts to 10-20 hours, while the duration can be reduced by re-washing the centrifuged crystallization product with n-heptane. The duration of drying can be reduced as well if the drying process is split into separate drying processes with a reduced loading of the dryer.

Homogenization of the dry cargo is required to ensure homogenous mixing and to chop the crystalline needles obtained from the crystallization process. Homogenization can be done in a mixer-dryer.

Under a mixer-dryer the person skilled in the art understands a dryer, which can be used both for drying as well as mixing of substances.

Suitable mixer-dryers for homogenization according to the present disclosure are dryers, for which a mantle temperature between 10° C. and 40° C. can be predefined. Preferred is a mantle temperature between 20-30° C. Particularly preferred is a mantle temperature of 20-25° C., e.g. of about 25° C.

A suitable mixer-dryer also enables stirring and chopping of the dry cargo. The dry cargo can be stirred with a speed between 1 and 10 rpm (starting with a stirring speed of 4 rpm constant movement of the stirring paddle is possible, at a lower speed it is possible that the paddle malfunctions to perpetuate the lower stirring speed), preferably between 4 and 6 rpm such as for example 4 rpm. Additionally, the dry cargo can be chopped or homogenized with a chopper using 100-800 rpm, preferably 200-400 rpm and particularly preferred 300 rpm. A universal dryer is a suitable mixer-dryer for homogenization of the dried Compound.

Drying on trays or shelves in a tray dryer under vacuum and subsequent homogenization in a universal dryer results in fine crystalline needles.

The process of homogenization requires adaptation to the instruments used, particularly the settings of the stirrer and the chopper. Additionally, the duration of the homogenization can vary between instruments used. However, homogenization preferably lasts less than 4 hours, e.g. 2 to 3 hours.

Surprisingly, it has been found that the bulk density of the dried compound seems to correlate with the dissolution rate. Usually, more sophisticated parameters, such as particle size distribution (PSD), is used for verification of process stability. However, for the present situation it emerged that simple bulk density measurements are more predictive with respect to dissolution predictability.

In this regard the product obtained from the reworking process can be characterized in that the Compound is dried and maintained a high degree of crystallinity and has a bulk density of 0.20 g/ml or lower, e.g. 0.15 g/mL or lower, e.g. ≤0.15 g/mL and ≥0.10 g/mL, e.g. ≤0.14 g/mL and ≥0.10 g/mL.

It should also be noted that the processability of the Compound is limited as milling leads to sticking and amorphization of the compound. No milling procedure could be identified that is robust and technically feasible on a commercially meaningful scale.

As mentioned above, the Compound (i.e. [5-(methylsulfonyl)-2-{[(2R)-1,1,1-trifluoropropan-2-yl]oxy}phenyl]{(1R,5R)-1-[5-(trifluoromethyl)-1,2-oxazol-3-yl]-3-azabicyclo[3.1.0]hex-3-yl}methanone) is described in example 50 of WO 2013/017657 as having the formula

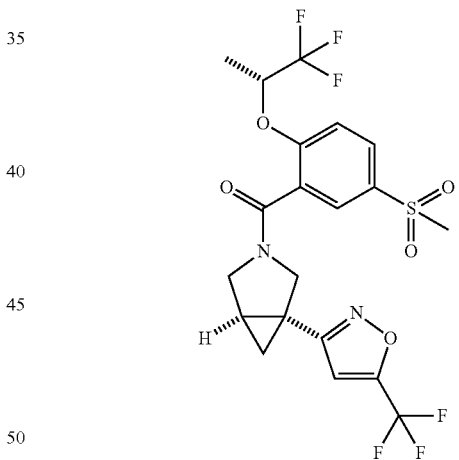

and being suitable for the treatment of a neurologic or psychiatric condition.

Accordingly, the reworked Compound of the invention can be used in or as a medicament. The Compound selectively inhibits glycine transporter-1 (GlyT1) which is for example of interest with respect to cognitive impairment associated with Schizophrenia or Alzheimer's disease. It can be used for the treatment of diseases which are accessible by GlyT1-inhibition, in particular sleep disorders like insomnia or narcolepsy, depression, substance use disorders/abuse disorders, hearing disorders, attention deficit (hyperactive) disorder, inflammatory pain, neuropathic pain, autism spectrum disorders or disorders of impulse control. Preferably, it can be used to treat illnesses such as psychoses, dysfunction in memory and learning, and schizophrenia (positive and negative symptoms of schizophrenia and cognitive impairment associated with schizophrenia).

Treatment comprises the administration of a therapeutically effective amount of the reworked Compound in a human being in need thereof.

Further Processing of the Dried Product

In another aspect the invention relates to further processing of the dried product to a blend, granules and tablets or tablet cores.

Dry Granulation

The compound is delivered to the drug product production unit in a non-milled, non-screened, agglomerated quality, as milling leads to sticking and amorphization of the compound. For the intended quality of the targeted-for drug product the dissolution performance (see above) and the uniformity of dosing units, according to pharmacopoeias is crucial. As dissolution performance is influenced by the above described drying variants, the uniformity of dosage units is dominated by the production process.

At the desired drug-load level (approx. 7% (w/w)) a stable and homogenous dispersion of the compound and the excipients is the quality critical aspect. A standard process to achieve a homogenous dispersion of solids in pharmacy is to screen and de-agglomerate all raw materials to approx. comparable particle sizes and subsequently blend the screened materials in a suitable pharma-blender (high or low shear). The standard process was not possible for the compound as it completely sticks to screens of standard pharma-mills and blocks the process. To overcome the sticking and amorphization tendencies of the compound during screening and milling a two-stepped pre-blend approach was developed.

As a first step the pre-weighted raw materials, the Compound, lactose monohydrate, microcrystalline cellulose, hydroxypropyl cellulose and croscarmellose sodium are placed in a suitable container and pre-blended using a suitable freefall blender to obtain a first technical pre-blend. In this pre-blend the agglomerates of the compound are roughly separated from each other and covered with the also added other raw-materials. (This separation allows a first gentle screening and deagglomeration of the compounds and the other materials.) The pre-blend is screened with a suitable screening mill using a coarse screen size of e.g. 3.2 mm (2.5-4.0 mm). As a result, 100% of the technical pre-blend passes the screen without blocking.

In a second step magnesium stearate is added to the screened pre-blend. This combination is then screened again using a suitable screening mill with a narrower screen size of e.g. 1.3 mm (0.8-2.0 mm). As a result, 100% of the pre-blend including magnesium stearate passes the screen without blocking.

The screened magnesium stearate/pre-blend combination is blended in a suitable freefall blender to obtain the fully de-agglomerated, homogenously dispersed pharmaceutical blend.

To fixate the homogenous dispersion of the compound and the excipients the blend is compressed with a suitable roller compactor (e.g. Hosokawa, or Gerteis, or other) into ribbons, which are immediately milled to granules by an integrated screening mill with a screen size of e.g. 1.0 mm (0.8-1.2 mm).

The produced granules can either be used as an intermediate process material for further compounding, or can be filled in capsules, sachets, or comparable dosing utilities to be used as drug product themselves.

Final Blending Prior to Compression to Tablets

To allow compression to tablets additional magnesium stearate and the granules (from the above granulation) are screened with a suitable screening mill using a screen size of e.g. 1.3 mm (0.8-2.0 mm).

The screened magnesium stearate/granules combination is blended in a suitable freefall blender to obtain the final blend.

Compression

The final blend is compressed into tablet cores using a standard rotary tablet press.

Film-Coating

The film-coating mixture is dispersed in water, purified using a suitable stirrer and vessel. Tablet cores are coated with the film-coating suspension in a suitable drum coater.

According to the above procedure, tablets have been prepared with qualitative and quantitative composition according to DF1 as shown further below.

Accordingly, the further aspect relates a process to obtain a de-agglomerated, homogenously dispersed pharmaceutical blend comprising the Compound, wherein the process comprises the following steps i) blending the Compound with one or more other ingredients, such as diluents and inert carriers,
ii) screening the pre-blend of step i) in a suitable equipment, e.g. screening mill, using a screen size of 2.5 to 4.0 mm,
iii) optionally adding a lubricant, preferably magnesium stearate, to the screened pre-blend obtained after step ii),
iv) screening the mixture of step iii) in a screening mill using a screen size of 0.8 to 2.0 mm,
v) optionally blending the screened lubricant/pre-blend combination.

In a further embodiment the above process further comprises the following steps (to obtain granules):

vi) compressing the blend of step v) into ribbons, and
vii) milling the ribbons to granules using a suitable equipment, e.g. a screening mill, with a screen size of 0.8 to 1.2 mm.

In a further embodiment the above process further comprises the following steps (to obtain tablets or tablet cores):

viii) screening the granules obtained from step vii), optionally together with lubricant, e.g. magnesium stearate, using a screening mill with a screen size of 0.8 to 2.0 mm,
ix) optionally blending the lubricant/granules combination,
x) compressing the blend of step ix) into tablets.

More specific embodiments of the process are defined below:

The screen size in step ii) is 3.0 to 3.4 mm.
The screen size in step iv) is 1.1 to 1.4 mm.
The screen size in step vii) is 0.9 to 1.1 mm.
The screen size in step viii) is 1.1 to 1.4 mm.
The other ingredients in step i) are selected from the group comprising lactose monohydrate, microcrystalline cellulose, and hydroxypropyl cellulose.
The other ingredients in step i) are selected from the group consisting of lactose monohydrate, microcrystalline cellulose, hydroxypropyl cellulose and croscarmellose sodium.

Further aspects relate to a blend obtained from the process or embodiments as described above.

Further aspects relate to granules obtained from the process or embodiments as described above.

Further aspects relate to granules obtained from the process or embodiments as described above, wherein the granules comprise lactose monohydrate, microcrystalline cellulose, hydroxypropyl cellulose and croscarmellose sodium.

Further aspects relate to a tablet or a tablet core obtained from the process or embodiments as described above.

Further aspects relate to a tablet or a tablet core obtained from the process or embodiments as described above, wherein the tablet or the tablet core comprise diluents and inert carriers selected from the group consisting of lactose monohydrate, microcrystalline cellulose, hydroxypropyl cellulose and croscarmellose sodium.

Further aspects relate to a tablet or a tablet core obtained from the process or embodiments as described above, wherein the tablet or the tablet core comprise 2 to 8% of the Compound, 50 to 70% lactose monohydrate, 20 to 30% microcrystalline cellulose, 2 to 10% hydroxypropyl cellulose, 1 to 5% croscarmellose sodium, and 0.8 to 2% magnesium stearate.

Further aspects relate to a tablet or a tablet core obtained from the process or embodiments as described above, wherein the tablet or the tablet core comprise 6 to 7% of the Compound, 55 to 60% lactose monohydrate, 22 to 27% microcrystalline cellulose, 4 to 6% hydroxypropyl cellulose, 2 to 4% croscarmellose sodium, and 1.0 to 1.5% magnesium stearate.

Pharmaceutical Composition

Suitable preparations for administering the reworked Compound of the invention will be apparent to those with ordinary skill in the art and include for example granules, tablets, pills and capsules. The content of the reworked Compound should be in the range from 0.05 to 90 wt.-%, preferably 0.1 to 50 wt.-% of the composition as a whole.

The reworked Compound for the use in the manufacture of pharmaceutical compositions as described herein may be in the form of polymorph I or II, including mixtures thereof.

Suitable tablets may be obtained, for example, by mixing the reworked Compound with known excipients, for example inert diluents such as calcium carbonate, calcium phosphate, lactose/lactose monohydrate, or microcrystalline cellulose; disintegrants such as maize starch, alginic acid or croscarmellose sodium; binders such as starch or gelatin; lubricants such as magnesium stearate or talc; and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly, the tablet coating may consist of a number or layers to achieve delayed release, possibly using the excipients mentioned above for the tablets.

For oral administration, the tablets may contain additives such as sodium citrate, calcium carbonate and dicalcium phosphate together with various additives such as starch, preferably potato starch, gelatin and the like. Moreover, lubricants such as magnesium stearate, sodium lauryl sulphate and talc may be used at the same time for the tabletting process. In the case of aqueous suspensions, the Compound may be combined with various flavour enhancers or colourings in addition to the excipients mentioned above.

Capsules containing the active substance of the invention, may, for example, be prepared by mixing the Compound with inert carriers such as lactose or sorbitol and packing them into gelatin capsules.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The invention also contemplates a pharmaceutical composition comprising at least two different polymorphs of the reworked Compound, e.g. polymorph I and polymorph II, and a pharmaceutically acceptable excipient.

The following specific examples of pharmaceutical dosage forms (DF1 and DF2) illustrate the present invention without restricting its scope:

DF1:

| Ingredients | 10 mg Dosage | | Function |
| --- | --- | --- | --- |
| | Quantity [%] | Mass [mg] | |
| The Compound | 6.90 | 10.00 | Active ingredient |
| Lactose monohydrate | 58.33 | 84.58 | Filler |
| Cellulose, microcrystalline | 25.52 | 37.00 | Filler |
| Hydroxypropyl cellulose | 5.00 | 7.25 | Binder |
| Croscarmellose sodium | 3.00 | 4.35 | Disintegrant |
| Magnesium stearate (intra granular) | 0.50 | 0.73 | Lubricant |
| Magnesium stearate (extra granular) | 0.75 | 1.09 | Lubricant |
| Total in % | 100 | 100 | — |
| Total weight of tablet core [mg] | | 145.00 | — |
| Film-coating mixture | 2.42 | 4.40 | Film-coating agent |
| Purified water | q.s. | q.s. | Solvent for film-coating suspension |
| Total in % | 100% | 100% | — |
| Total weight of film-coated tablet [mg] | | 149.40 | — |

Film-Coating Mixture, e.g.:

| Excipient | Quantity | Function |
| --- | --- | --- |
| Hypromellose | 50.000% | Film former |
| Macrogol 400 | 5.000% | Plasticizer |
| Talc | 15.000% | Anti-adherent |
| Titanium dioxide | 25.000% | Pigment |
| Iron oxide yellow | 2.500% | Pigment |
| Iron oxide red | 2.500% | Pigment |

DF2:

|  | Ingredients | 1 mg | | 25 mg | |
|---|---|---|---|---|---|
|  |  | mg/per tablet | % (w/w) | mg/per tablet | % (w/w) |
|  | Granulation (Intra-granular) | | | | |
| (1) | The Compound | 1.0 | 1.25 | 25.0 | 6.25 |
| (2) | Lactose, Monohydrate NF, Modified Agglomerated | 26.20 | 32.75 | 121.80 | 30.45 |
| (3) | Microcrystalline Cellulose, Type 102 SCG | 24.80 | 31.00 | 118.60 | 29.65 |
| (4) | Croscarmellose Sodium | 2.40 | 3.00 | 12.0 | 3.00 |
| (5) | Magnesium Stearate, Vegetable Grade | 0.40 | 0.50 | 2.0 | 0.50 |
|  | Blending (Extra-granular) | | | | |
| (6) | Microcrystalline Cellulose, Type 102 SCG | 24.80 | 31.00 | 118.60 | 29.65 |
| (7) | Magnesium Stearate, Vegetable Grade | 0.40 | 0.50 | 2.0 | 0.50 |
|  | Total | 80 mg | 100% | 400 mg | 100% |

EXAMPLES

Example 1A: Preparation of a Mixture of Polymorph I and II of the Compound

A reactor is charged with the amorphous form of the Compound (20 g) and 2-propanol (75 mL) and the contents are heated to 70° C. The resulting solution is treated with water (111 mL) while maintaining a batch temperature of not less than 50° C. The reactor contents are then cooled to 20° C. over 1.5 hr. The solids are collected by filtration, rinsed with water, and dried under reduced pressure at 40° C. to provide a mixture of Form I and Form II of the Compound (15.4 g, 77% yield) having a molar ratio of 61:39 (Form I:Form II).

Example 1B: Preparation of Polymorph I (Form I) of the Compound

Amorphous Compound (50 mg) is treated with 4 ml of tert-butyl methyl ether (TBME) and the resulting slurry is stirred for 2 h at 50° C. About 2 ml of solvent is removed under reduced pressure. The mixture is then filtered, and the solids dried overnight in a vacuum oven at 40° C. to provide Form I of the Compound.

Form I of the Compound can also be prepared according to the procedure described immediately above using water instead of TBME.

Example 2A: Preparation of Polymorph II (Form II) of the Compound

A reactor is charged with a mixture of Form I and Form II of the Compound (37 g, 0.072 mol) and 140 ml of isopropanol, and the reactor contents are heated to about 70° C. The resulting solution is vacuum filtered (Buchner funnel equipped with filter paper) and the filtrate cooled to about 55° C. The solution is then treated with water (111 mL) and seeded with 0.74 g of Form II of the Compound while being rigorously mixed at 55° C. for at least 4 hours. Additional water (95.14 g) is added to the stirred mixture over at least 6 hours, the agitation is stopped, and the reactor contents are cooled to 20° C. over at least 4 hours. The resulting solids are then collected by filtration, washed with water and then heptane and air-dried to provide Form II of the Compound.

Example 2B: Preparation of Polymorph II (Form II) of the Compound

A reactor is charged with a mixture of Form I and Form II of the Compound (100 g, 0.195 mol), isopropanol (500 ml) and water (100 ml). The reactor contents are heated with stirring to 55-60° C. and the resulting solution is vacuum filtered (Buchner funnel equipped with filter paper) at 55-60° C. The stirred filtrate is heated to 68-70° C., treated with 600 mL of water while maintaining the temperature at 68-70° C., and cooled to 62-66° C. over 30 min. The solution is seeded with a seed slurry of Form II of the Compound (2 g) in mixture of 20 g of water and 4 g of isopropyl alcohol, aged at 62-66° C. for 0.5 h, and cooled to 55° C. over 2-3 hrs. The resulting mixture is stirred at 55° C. for 2 hr, cooled to 20° C. over 4-6 hr, and filtered. The solids are washed with water (200 mL) and dried at 50-70° C. for at least 8 hr to provide Form II of the Compound.

Example 3: Preparation of Polymorph III of the Compound

A reactor is charged with Form II of the Compound (20 g, 39 mmol) and methanol (200 mL), and the reactor contents are heated to 50-55° C. The reactor contents are then concentrated under reduced pressure at 40-45° C. to approximately 80 ml, cooled to room temperature over at least 1 hour, and stirred for an additional 2 hours at room temperature. The solids are collected by filtration, washed with heptane, and dried under reduced pressure at 50° C. for 10 hours to provide 19.46 g of Form III of the Compound.

Example 4: Recrystallization of the Compound 20.0 g of the Compound are suspended in a mixture of 98.7 g isopropanol and 167.7 g water. Subsequently the suspension is dissolved at 70-80° C., stirred for 15-30 minutes at this temperature and then vacuum-filtrated. The solution obtained is tempered to 54-60° C. 600 mg seeding crystals are added and stirred for 4 hours at 54-60° C. Subsequently the temperature is lowered to 30-40° C. for 90-110 minutes and the resulting suspension is stirred for 30-45 minutes at this temperature. For ageing of the crystals, the material is warmed to 54-60° C. again, stirred for 30-45 minutes and subsequently cooled for a period of 90-110 minutes to 30-40° C. The suspension is filtered, and the crystallization product obtained washed with 58.0 g water and 82.0 g n-heptane.

Example 5: Drying of Batches 17102-17204 in a Universal Dryer

Batch 17102 was obtained by inoculation of a solution of the Compound in Isopropanol/water. The precipitated product was isolated as moist product by centrifugation and washed with 35° C. warm water.

Batch 17103 and 17104 was obtained by inoculation of a solution of the Compound in Isopropanol/water. The precipitated product was isolated as moist product by centrifugation, washed with purified water at first and subsequently with n-heptane.

Batches 17101, 17102, 17103 and 17104 (the crystallization product) of the Compound were reworked in a paddle-dryer as summarized in Table 7. The dryer device used was a universal dryer of the manufacturer Rosemund.

Settings of the used universal dryer were:
Mantle temperature: 50° C.
Paddle: 4 rpm
Carrier gas: off
Vacuum: on (resulting in effective pressure of about 30 to 70 mbar)
Chopper: off at the outset
  for batch 17101 the chopper was turned on after 12 hours drying time at 300 rpm
  for batch 17102 the chopper was turned on after 1 hour drying time at 300 rpm
  for batch 17103 the chopper was turned on twice for about 10 minutes
  for batch 17104 the chopper was turned on once for about 10 minutes
Drying was terminated, if in a halogen dryer a loss of drying ≤0.5% was ascertained in a sample taken at 110° C. To reduce the drying time of the batches 17103 and 17104 the crystallization product was re-washed after centrifugation with n-heptane. Additionally, the drying process was split into separate processes with a reduced loading of the dryer.

TABLE 7

Drying conditions of batches 17101-17104 in a universal dryer

| Batch | 17101 | 17102 | 17103 | 17104 |
|---|---|---|---|---|
| Amount of isolated product | 31.0 kg | 40.6 kg | 18.0 kg | 13.3 kg |
| Washing solvent | Water | Water | water/n-heptane | water/n-heptane |
| Bulk density | | 280 g/L | | |
| Drying duration | 23 h | 32 h | 19 h | 7.5 h |
| Mantle-temperature | | 50° C. | | |
| Paddle | | on | | |
| Chopper | on after 12 h 300 rpm | on after 1 h 300 rpm | on 2x 10 min 300 rpm | on 1x 10 min 300 rpm |
| Carrier gas | | off | | |
| Bulk density [g/mL] | n/a | 0.35 | 0.50 | 0.23 |

The first two batches (17101, 17102) were exclusively washed with water and the drying process lasted up to 32 hours. The material exhibited strong agglomeration and the scanning electron microscope disclosed melted cores of the agglomerates.

To reduce the load in the dryer, the centrifugation and drying of the third batch was divided in two separate isolations. After the first half of the batch was centrifuged (17103) the material was still quite moist. During the drying process larger agglomerates were formed, which, however, did not show a melted core. After centrifugation and drying of the second half of the batch (17104) only loose agglomerates were formed, which could be easily crushed.

All batches were processed to tablets according to Example 8. The results of the dissolution tests (Example 9) were below the dissolution achieved with material dried in a tray dryer (see Table 11).

Example 6: Drying of Batches 1-4TA and 1-4 TB in a Universal Dryer

By inoculation of a solution of the Compound in Isopropanol/water precipitated product was isolated (Example 4) as moist product by centrifugation, at first washed with purified water and then with n-heptane and reworked in a mixer-dryer as summarized in Table 8.

Improving the crystallization process of the crystallization product leads to a better spinning of the crystallization product, which reduces the residual moisture content after centrifugation. Reduced residual moisture reduces the duration of the drying process.

Drying was done in a universal dryer first at 65° C. without stirring (the paddle is only turned on for filling the dryer and withdrawing of a sample) until a loss of drying of ≤5% was achieved. Then the mantle temperature of the universal dryer was reduced to 50° C. and the paddle was turned on until a loss of drying of ≤0.5% was achieved. Finally, the mantle temperature of the universal dryer was reduced to 20° C. before homogenization in the presence of stirring (4 rpm) and chopping (300 rpm) started.

Batches 1-4 TA and 1-4 TB of the crystallization product were reworked in a mixer-dryer as summarized in Table 8.

Drying Step 1 (DS1):
  Mantle temperature: 65° C.
  Paddle: turned on only for filling the dryer and withdrawing a sample
  Filling up to a reduced degree of filling
  After filling the paddle is turned off
  Chopper: off
  Carrier gas: on
  Vacuum: on (resulting effective pressure of about 30 to 70 mbar)
  To withdraw a sample the paddle must be turned on briefly and turned off afterwards
  As soon as in a withdrawn sample a loss of drying of ≤5% is determined at a temperature of 110° C. in a halogen dryer, paddle and chopper are turned on, and the mantel temperature is reduced (50° C.).

Drying Step 2 (DS2):
  Mantle temperature: 50° C.
  Paddle: 4 rpm
  Chopper: off
  Carrier gas: on
  Vacuum: on (resulting effective pressure of about 30 to 70 mbar)
  Drying step 2 is terminated, once for a withdrawn sample a loss of drying of ≤0.5% is determined in a halogen dryer at a temperature of 110° C.
  Finally, mantle heating is turned off and the material is cooled to ≤25° C. then the material is homogenized while stirring and chopping Homogenization (H):
  Mantle temperature: 20° C.
  Paddle: 4 rpm
  Chopper: 300 rpm
  Carrier gas: off
  Duration: 2-3 hours Four batches (1-4) were prepared with two separate drying processes (TA and TB) and dried in a universal dryer applying improved conditions.

TABLE 8

Improved drying conditions in a universal dryer

| Batch | 1TA | 1TB | 2TA | 2TB | 3TA | 3TB | 4TA | 4TB |
|---|---|---|---|---|---|---|---|---|
| Amount of isolated product | 17.6 kg | 24.4 kg | 29.7 kg | 25.2 kg | 27.4 kg | 25.9 kg | 22.8 kg | 29.7 kg |
| Washing solvent | water/n-heptane | | | | | | | |
| Mantle temperature:<br>Drying duration | DS1. 65° C.:<br>251 min<br>DS2. 50° C.:<br>136 min<br>H 20° C.:<br>180 min | DS1. 65° C.:<br>273 min<br>DS2. 50° C.:<br>149 min<br>H. 20° C.:<br>180 min | DS1. 65° C.:<br>447 min<br>DS2. 50° C.:<br>230 min<br>H. 20° C.:<br>180 min | DS1. 65° C.:<br>350 min<br>DS2. 50° C.:<br>230 min<br>H. 20° C.:<br>180 min | DS1. 65° C.:<br>494 min<br>DS2. 50° C.:<br>203 min<br>H. 20° C.:<br>180 min | DS1. 65° C.:<br>448 min<br>DS2. 50° C.:<br>212 min<br>H. 20° C.:<br>180 min | DS1. 65° C.:<br>1120 min<br>DS2. 50° C.:<br>254 min<br>H. 20° C.:<br>177 min | DS1. 65° C.:<br>372 min<br>DS2. 50° C.:<br>293 min<br>H. 20° C.:<br>172 min |
| Paddle on/off and rpm | DS1: only on when filling and sampling<br>DS2: on, 4 rpm<br>H: on, 4 rpm | | | | | | | |
| Chopper speed | Only on when homogenizing, at 300 rpm | | | | | | | |
| Vacuum | On | | | | | | | |
| Carrier gas | On | | | | | | | |
| Bulk density [g/mL] | 0.17 | 0.16 | 0.17 | 0.2 | 0.18 | 0.17 | 0.22 | 0.17 |

DS1: Drying Step 1;
DS2: Drying Step 2;
H: Homogenization

The drying process was conducted for all 8 batches under the same conditions. (Drying time is determined by residual water content.) The substance was not agitated in moist condition (except when filling or sampling). DP dissolution data of the batches, however, showed a high variability and there was no consistent result for all eight batches. The drying process in a universal dryer is, therefore, not rated robust.

Example 7-1: Drying on Shelves in a Vacuum Tray Dryer with Subsequent Homogenization in a Universal Dryer Settings of the Vacuum Tray Dryer:
  Mantle temperature: 65° C.
  Carrier gas: on
  Vacuum: on
  Termination of drying: upon detection in a sample a loss of drying at 110° C. of ≤0.5% with a halogen dryer
Settings of the Universal Dryer for Homogenization:
  Mantle temperature: 20° C.
  Paddle: 4 rpm
  Chopper: 200-400 rpm
  Carrier gas: off
  Duration of homogenization: 2-3 h.

TABLE 9

Drying conditions on trays in a vacuum tray dryer and subsequent subsequent homogenization in a universal dryer

| Batch | 18105 | 18106 | 18107 | 5 | 6 |
|---|---|---|---|---|---|
| Amount of isolated product | 15.9 kg | 23.0 kg | 21.9 kg | 43.2 kg | 43.1 kg |
| Washing solvent | water/n-heptane | | | | |
| Drying duration | 14 h | 20 h | 10.5 h | 12.75 h | 12.5 h |
| Mantle temp. | 65° C. | | | | |
| Carrier gas | on | | | | |
| Homogenization duration | 180 min | 143 min | 215 min | 170 min | 145 min |
| Bulk densitiy [g/mL] | 0.12 | 0.15 | 0.14 | 0.14 | 0.15 |

Drying of the different batches on shelves of a tray dryer and subsequent homogenization in a universal dryer yielded the reworked Compound as fine crystalline needles. Tablets produced therefrom showed good and consistent solubility. DP dissolution after 45 minutes was consistently between 95-99% (see Table 10).

Example 7-2: Drying on Shelves in a Vacuum Tray Dryer with Subsequent Homogenization in a Universal Dryer and Screening Settings of the Vacuum Tray Dryer:
  Mantle temperature: 60° C.
  Vacuum: on
  Termination of drying: upon detection in a sample a loss of drying at 110° C. of ≤0.5% with a halogen dryer
Settings of the Universal Dryer for Homogenization:
  Mantle temperature: 20° C.
  Paddle: 4 rpm
  Chopper: 200-400 rpm
  Carrier gas: off
  Duration of homogenization: 2 h 30 min-3 h 20 min.
Settings of Screening Using a Conical Sieve Mill ("ConiWitt 150" from Frewitt)
  Sieve inserts: 5 mm square openings and 4 mm round openings

| Batch 109- | 8942 | 8943 | 9100 | 8955 | 9101 | 9102 | 9103 | 9104 | 8954 |
|---|---|---|---|---|---|---|---|---|---|
| Amount of isolated product [kg] | 52.6 | 67.7 | 82.6 | 81.6 | 52.1 | 44.7 | 53.5 | 50.5 | 76.7 |
| Washing solvent | | | | water/n-heptane | | | | | |
| Drying duration | 22 h | 21 h | 22 h | 21 h | 13 h | 11 h | 12 h | 13 h | 21 h |
| Mantle temp. | | | | | 60° C. | | | | |
| Homogenization duration | | | | 2 h 30 min-3 h 20 min | | | | | |
| screening | yes | yes | yes | yes | yes | yes | yes | yes | yes |
| Bulk density [g/mL] | 0.16 | 0.14 | 0.15 | 0.15 | 0.14 | 0.15 | 0.15 | 0.15 | 0.15 |

Example 8: Processing of the Dried Product to Tablets

Manufacture of Granules (Step 1)
  The Compound, lactose monohydrate, microcrystalline cellulose, hydroxypropyl cellulose and croscarmellose sodium are pre-blended in a suitable freefall blender to obtain the pre-blend (step 1.1).
  The pre-blend is screened with a suitable screening mill using a screen size of 3.2 mm (step 1.2).
  Magnesium stearate and the screened pre-blend (from step 1.2) are then screened using a suitable screening mill with a screen size of 1.3 mm (step 1.3).
  The screened magnesium stearate/pre-blend combination is blended in a suitable freefall blender to obtain the blend (step 1.4).
  The blend is compressed with a suitable roller compactor into ribbons, which are screened by an integrated screening mill with a screen size of 1.0 mm into granules (step 1.5).
Manufacture of Final Blend (Step 2)
  Magnesium stearate and granules (from step 1.5) are screened with a suitable screening mill using a screen size of 1.3 mm (step 2.1).
  The screened magnesium stearate/granules combination is blended in a suitable freefall blender to obtain the final blend (step 2.2).

Manufacture of Tablet Cores (Step 3)
  The final blend (from step 2.2) is compressed into tablet cores using a standard rotary tablet press.
Manufacture of Film-Coated Tablets (Step 4)
  The film-coating mixture is dispersed in purified water by stirring in a suitable mixing vessel (step 4.1).
  The tablet cores are coated with the film-coating suspension (from step 4.1) in a suitable drum coater to produce film-coated tablets containing the Compound.
  According to the above procedure, tablets have been prepared with qualitative and quantitative composition according to DF1 as shown above in batch sizes of 5 to 120 kg. The process seems suitable for even larger batch sizes.

Example 9: Measurement of the Release/Dissolution Behavior of the Dried Crystallization Product (Drug Product Dissolution) from Tablets Obtained According to Example 8

For a period of 90 minutes tablets are dissolved in 900 ml medium consisting of 0.1M HCl with 0.25% sodium dodecylsulfate (SDS) using a paddle mixer apparatus Dissolution test for solid dosage forms, Apparatus 2), while a stirring speed of 75 rpm is applied. Samples are taken at the points of time detailed using a Toyama Fine Filters F-25. During the last 30 minutes of the test the stirring speed is increased to 1590 rpm. Release of the Compound is quantified with an HPLC/UV-method.

Tables 10 provides indication, that drying on shelves in a tray dryer results in improved (DP)-dissolution behavior, e.g. in increased dissolution rate or providing consistently high dissolution rates independent of small process variations during drying and homogenization.

TABLE 10-1

| | iGlyT1 DS | DP lot # | Disso % 5 min | Disso % 10 min | Disso % 15 min | Disso % 20 min | Disso % 30 min | Disso % 45 min | Disso % 60 min | Disso % 90 min (infinity) |
|---|---|---|---|---|---|---|---|---|---|---|
| Agitated drying in a universal dryer | 17101 | X180121 | 63 | 72 | 76 | 79 | 82 | 85 | 87 | 91 |
| | 17102 | X180102 | 50 | 58 | 62 | 65 | 70 | 74 | 77 | 83 |
| | 17103 | X180122 | 64 | 72 | 76 | 78 | 81 | 83 | 85 | 88 |
| | 17104 | X180104 | 70 | 77 | 80 | 82 | 85 | 88 | 89 | 93 |
| | 1 TA | X180207 | 72 | 80 | 84 | 86 | 88 | 90 | 91 | 93 |
| | 1 TB | X180208 | 69 | 83 | 87 | 89 | 92 | 94 | 95 | 96 |
| | 2 TA | X180209 | 72 | 80 | 85 | 87 | 89 | 92 | 93 | 94 |
| | 2 TB | X180210 | 60 | 71 | 76 | 78 | 82 | 84 | 86 | 89 |
| | 3 TA | X180211 | 73 | 82 | 86 | 89 | 91 | 93 | 94 | 95 |
| | 3 TB | X180212 | 75 | 86 | 91 | 94 | 96 | 98 | 99 | 100 |
| | 4 TA | X180213 | 63 | 72 | 75 | 78 | 81 | 83 | 85 | 88 |
| | 4 TB | X180214 | 74 | 83 | 87 | 90 | 93 | 95 | 96 | 97 |
| Drying on shelves in a vacuum tray dryer with subsequent homogenization | 18105 | X180081 | 78 | 87 | 91 | 93 | 96 | 97 | 98 | 99 |
| | 18106 | X180082 | 74 | 84 | 89 | 91 | 94 | 96 | 96 | 98 |
| | 18107 | X180083 | 76 | 86 | 91 | 94 | 96 | 98 | 98 | 100 |
| | 5 | X180227 | 81 | 89 | 92 | 94 | 96 | 97 | 97 | 98 |
| | 6 | X180228 | 80 | 88 | 91 | 93 | 95 | 96 | 96 | 97 |

TABLE 10-2

| | iGlyT1 DS | DP lot # | Disso % 5 min | Disso % 10 min | Disso % 15 min | Disso % 20 min | Disso % 30 min | Disso % 45 min | Disso % 60 min | Disso % 90 min (infinity) |
|---|---|---|---|---|---|---|---|---|---|---|
| Drying on shelves in a tray vacuum dryer with subsequent homogenization and screening | 1098942 | X200190 | 77 | 85 | 89 | 90 | 93 | 94 | 95 | 96 |
| | 1098943 | X200191 | 74 | 85 | 90 | 92 | 94 | 96 | 96 | 97 |
| | 1099100 | X200188 | 74 | 83 | 87 | 89 | 91 | 93 | 93 | 95 |
| | 1098955 | X200193 | 76 | 84 | 88 | 89 | 91 | 93 | 94 | 96 |
| | 1099101 | X200194 | 70 | 81 | 86 | 89 | 92 | 93 | 94 | 97 |
| | 1099102 | X200197 | 77 | 87 | 91 | 93 | 95 | 97 | 98 | 98 |
| | 1099103 | X200195 | 77 | 87 | 91 | 93 | 96 | 97 | 98 | 99 |
| | 1099104 | X200196 | 77 | 86 | 90 | 91 | 93 | 95 | 96 | 97 |
| | 1098954 | X200192 | 74 | 84 | 88 | 90 | 93 | 95 | 95 | 96 |

Fine crystalline needles were obtained. Tablets produced therefrom showed good and consistent solubility. DP dissolution after 45 minutes was between 93-97%.

The invention claimed is:

1. A process of reworking a crystalline compound of formula (I)

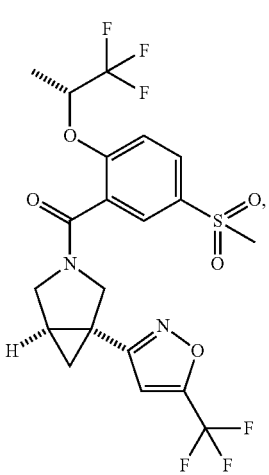

(I)

the process comprising:
i) drying a crystalline compound (I) in a tray dryer or in a pan dryer to provide a dry form of crystalline compound (I) having:
characteristic X-ray reflections at the following 2Θ values:
4.1°, 4.6°, 10.0°, 16.7°, and 18.0°; or
characteristic $^{13}C$ solid-state NMR chemical shifts selected from: 130.1 ppm, 46.6 ppm, and 25.0 ppm; or
at least three characteristic $^{19}F$ solid-state nuclear magnetic resonance peaks at chemical shifts selected from −64.0, −65.6, −66.6, −78.2, and −79.1 ppm, and
ii) homogenizing the dry form of crystalline compound (I) from step (i), to provide a reworked form of crystalline compound (I).

2. The process of claim 1, wherein drying step i) is performed in the presence of a carrier gas which is argon or nitrogen.

3. The process claim 1, wherein the homogenization in step ii) is performed in a mixer-dryer.

4. The process of claim 1, further comprising the following steps to produce the crystalline compound (I) used in step i):
(a) heating a mixture of compound (I) in a suitable solvent to 70° C. to provide a solution;
(b) filtering the solution of step (a);
(c) cooling the filtrate from step (b) to 55° C.;

(d) treating the cooled solution of step (c) with water;
(e) cooling the water-treated mixture of step (d) to 20° C.; and
(f) collecting the resulting crystalline compound (I).

5. The process of claim 1, further comprising the steps of
iii) blending the reworked form of crystalline compound (I) from step ii) with one or more other ingredients,
iv) screening the pre-blend of step iii) in a suitable equipment using a screen size of 2.5 to 4.0 mm,
v) optionally adding a lubricant, preferably magnesium stearate, to the screened pre-blend obtained after step iv),
vi) screening the mixture of step iv) or v) in a screening mill using a screen size of 0.8 to 2.0 mm,
vii) optionally blending the screened lubricant/pre-blend combination
to obtain a de-agglomerated, homogenously dispersed pharmaceutical blend.

6. The process of claim 5 further comprising the steps of
viii) compressing the blend of step vii) into ribbons, and
ix) milling the ribbons to granules using a suitable equipment with a screen size of 0.8 to 1.2 mm to obtain granules.

7. The process of claim 6 further comprising the steps of
x) screening the granules obtained from step ix), optionally together with a lubricant using a screening mill with a screen size of 0.8 to 2.0 mm,
xi) optionally blending the lubricant/granules combination,
xii) compressing the blend of step x) or xi) into tablets or tablet cores.

* * * * *